(12) United States Patent
Gillberg et al.

(10) Patent No.: US 6,393,316 B1
(45) Date of Patent: May 21, 2002

(54) METHOD AND APPARATUS FOR DETECTION AND TREATMENT OF CARDIAC ARRHYTHMIAS

(75) Inventors: Jeffrey J. Gillberg, Coon Rapids; Lev A. Koyrakh, Plymouth, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/566,477

(22) Filed: May 8, 2000

Related U.S. Application Data
(60) Provisional application No. 60/133,739, filed on May 12, 1999.

(51) Int. Cl.[7] .................................................. A61N 5/04
(52) U.S. Cl. ............................ 600/515; 607/5; 600/518
(58) Field of Search ................................. 600/513, 515, 600/510, 518, 511, 521; 607/4, 5

(56) References Cited

U.S. PATENT DOCUMENTS

| | | | |
|---|---|---|---|
| 4,375,817 A | 3/1983 | Engle et al. | 128/419 D |
| 4,384,585 A | 5/1983 | Zipes | 128/419 D |
| 4,548,209 A | 10/1985 | Wielders et al. | 128/419 D |
| 4,587,970 A | 5/1986 | Holley et al. | 128/419 PG |
| 4,693,253 A | 9/1987 | Adams | 128/419 D |
| 4,726,380 A | 2/1988 | Vollmann et al. | 128/419 PG |
| 4,800,883 A | 1/1989 | Winstrom | 128/419 D |
| 4,819,643 A | 4/1989 | Menken | 128/419 P |
| 4,830,006 A | 5/1989 | Haluska et al. | 128/419 PG |
| 4,880,004 A | 11/1989 | Baker, Jr. et al. | 128/419 PG |
| 4,880,005 A | 11/1989 | Pless et al. | 128/419 PG |
| 4,949,719 A | 8/1990 | Pless et al. | 128/419 D |
| 4,949,730 A | 8/1990 | Cobben et al. | 128/775 |
| 4,953,551 A | 9/1990 | Mehra et al. | 128/419 D |
| 5,117,824 A | 6/1992 | Keimel et al. | 128/419 D |
| 5,163,427 A | 11/1992 | Keimel | 128/419 D |
| 5,188,105 A | 2/1993 | Keimel | 128/419 D |
| 5,312,441 A | 5/1994 | Mader et al. | 607/5 |
| 5,471,991 A | 12/1995 | Shinnar | 128/705 |
| 5,755,736 A | 5/1998 | Gillberg et al. | 607/4 |
| 5,991,656 A | 11/1999 | Olson et al. | 607/4 |

OTHER PUBLICATIONS

Walter H. Olson et al., "Onset and Stability for Ventricular Tachyarrhythmia Detection in an Implantable Pacer–Cardio-verter–Defibrillator" *Computers in Cardiology*, Oct. 7–10, 1986, Boston, MA IEEE Computer Society Press; 167–170.
Thakor, Nitish V., "Reliable R–Wave Detection From Ambulatory Subjects" *Biomedical Sciences Instrumentation*, vol. 14, 1978, pp. 67–72.
Walter, James S., *A Primer on Wavelets and Their Scientific Applications*, Chapter I, Chapman and Hall/CRC, pp. 1–9.

*Primary Examiner*—Jeffrey R. Jastrzab
*Assistant Examiner*—Frances P. Oropeza
(74) *Attorney, Agent, or Firm*—Girma Wolde-Michael

(57) ABSTRACT

A device for monitoring heart rhythms. The device is provided with an amplifier for receiving electrogram signals, a memory for storing digitized electrogram segments including signals indicative of depolarizations of a chamber or chamber of a patient's heart and a microprocessor and associated software for transforming analyzing the digitized signals. The digitized signals are analyzed by first transforming the signals into signal wavelet coefficients using a wavelet transform. The higher amplitude ones of the signal wavelet coefficients are identified and the higher amplitude ones of the signal wavelet coefficients are compared with a corresponding set of template wavelet coefficients derived from signals indicative of a heart depolarization of known type. The digitized signals may be transformed using a Haar wavelet transform to obtain the signal wavelet coefficients, and the transformed signals may be filtered by deleting lower amplitude ones of the signal wavelet coefficients. The transformed signals may be compared by ordering the signal and template wavelet coefficients by absolute amplitude and comparing the orders of the signal and template wavelet coefficients. Alternatively, the transformed signals may be compared by calculating distances between the signal and wavelet coefficients. In preferred embodiments the Haar transform may be a simplified transform which also emphasizes the signal contribution of the wider wavelet coefficients.

38 Claims, 11 Drawing Sheets

METHOD AND APPARATUS FOR DETECTION AND TREATMENT OF CARDIAC ARRHYTHMIAS

This application claims priority from U.S. Provisional Patent Application No. 60/133,739 filed May 12, 1999, incorporated herein by reference in its entirety.

BACKGROUND OF THE INVENTION

This invention relates to implantable monitors and stimulators generally and more particularly to implantable heart monitors and heart stimulators, such as implantable cardioverter/defibrillators (ICDs).

One of the problems addressed in the design of implantable ICDs is the avoidance of unnecessary electrical shocks delivered to a patient's heart in response to rapid heart rates caused by exercise (sinus tachycardia) or by atrial fibrillation. Such rhythms are known collectively as supraventricular tachycardias (SVTs). Studies have shown that SVTs may occur in up to 30% of ICD patients. In theory, the shape of the QRS complex in the EGM signal during SVT will not change significantly in most patients, because ventricular depolarizations are caused by normal HIS-Purkinje conduction from the atrium to the ventricle. If high ventricular rates are due to a ventricular tachycardia (VT), one can expect a very different morphology of the electrogram (EGM) signal of the ventricular depolarization (QRS complex) because of a different pattern of electrical activity of the heart during VT. The question thus arises of how to distinguish normal QRS complexes present during SVTs from those indicative of a VT.

One approach to this problem is to study the morphology of the QRS complex and discriminate normal heart beats from abnormal ones based on the similarity of the signal to a sample waveform recorded from the normal heartbeat. The sample waveform is typically referred to as a template. One of the existing methods to discriminate between VT and normal EGM waveforms is based on the properly measured width of the QRS complex. A normal QRS complex is generally narrower than the QRS complex during VT. However there are cases when an abnormal (VT) QRS complex will have a different morphology while remaining narrow. In those cases a more sensitive and selective method is needed to discriminate between different waveforms. The common approach for such morphology analysis is Correlation Waveform Analysis (CWA) or its less computationally costly counterpart, so-called Area of Difference Analysis (AD). Both require minimization of a function describing difference between two signals (sum of squared differences of wave data points for the case of CWA, and the sum of absolute values of the differences for AD). However such computations as typically performed are more computationally costly and require more power than is generally desirable within implantable ICDs.

SUMMARY OF THE INVENTION

The present invention comprises a method and apparatus for reliable discrimination between ventricular depolarizations resulting from normal and abnormal propagation of depolarization wavefronts through the chambers of a patient' heart by means of a wavelet transform based method of analysis of depolarization waveforms. The use of the wavelet transformation based morphology analysis method of the present invention significantly reduces the amount of computation necessary to perform the task. It also performs de-noising of the signal at no additional cost. The present invention may also be used to discriminate between other waveform types, for example, between normal and aberrantly conducted depolarizations of the atrium. The specific embodiments disclosed below, however, are directed toward distinguishing normal and aberrantly conducted ventricular depolarizations.

Three embodiments of wavelet based morphology analysis methods according to the present invention are described in more detail below. A first disclosed embodiment compares template and unknown waveforms in the wavelet domain by ordering wavelet coefficients of the template and unknown waveforms by absolute amplitude and comparing the resulting orders of the coefficients. The second and third disclosed embodiments perform analogs of CWA and AD computations in the wavelet domain. All three methods produce good discrimination of QRS complexes during VTs from normal QRS complexes during SVTs and may be readily implemented in the embedded environments of implantable ICDs. It is believed the embodiments disclosed may also be usefully applied to discriminate between other waveform types, as discussed above.

The wavelet transform is a representation of a signal as a sum of so-called wavelets or little waves. The wavelets are highly localized in time or in the mathematical language, have compact support. The main difference between the wavelet functions used in wavelet transforms and the sine and cosine functions used in the Fourier transform is that wavelets have limited support that scales exponentially. Because of this exponential scaling, wavelet coefficients carry information about time scales present in the signal at various times. Also, wavelets form an orthogonal basis, and in the cases considered in the context of the present invention, these bases are complete, meaning that there are exactly as many wavelets as needed to represent any signal.

There are certain computational advantages of using wavelet transforms instead of Fourier transforms. The wavelet transform will usually yield a small number of coefficients that are adequate to accurately represent the original signal, and thus will achieve a high degree of information compression. This can be especially important for implantable monitors and stimulators because the information compression provided can be employed to substantially reduce the number of required computations. By leaving a small number of wavelet coefficients intact and deleting the rest of them by setting them to zero, the signal can also be efficiently filtered and de-noised.

The gold standard for comparison of waveform morphologies is the correlation waveform analysis (CWA) method, which is based on computation of the correlation function between two waves. However, the computational price of the correlation function is quite high, which makes it undesirable for use in implantable ICDs, which typically employ an 8 or 16 bit CPU running at about 1 MHz clock speed. If one wants the morphology analysis to be independent of the wave amplitude using traditional CWA methodologies, for example, then a 50 sample QRS complex waveform would require normalization at all 50 data points, which would involve 50 integer multiplications and divisions. The traditional correlation function computation will further require calculation of 50 squares and multiple long additions. On the other hand, if one performs this computation in the wavelet domain according to the second and third methods of the present invention, the number of values requiring normalization may be only 10 to 20. Additional reductions in required computations can be obtained by means of a simplified wavelet image comparison methodology according to the first embodiment of the present invention referred to above. Alternative embodiments of the invention apply the so-called Area of Difference approach (AD) or the CWA metric to the selected normalized values derived from the wavelet transform.

BRIEF DESCRIPTION OF THE DRAWINGS

The above and still further objects, features and advantages of the present invention will become apparent from the following detailed description of an exemplary preferred embodiment, taken in conjunction with the accompanying drawings, and, in which.

DETAILED DESCRIPTION OF THE PREFERRED EMBODIMENTS

Figure 1:
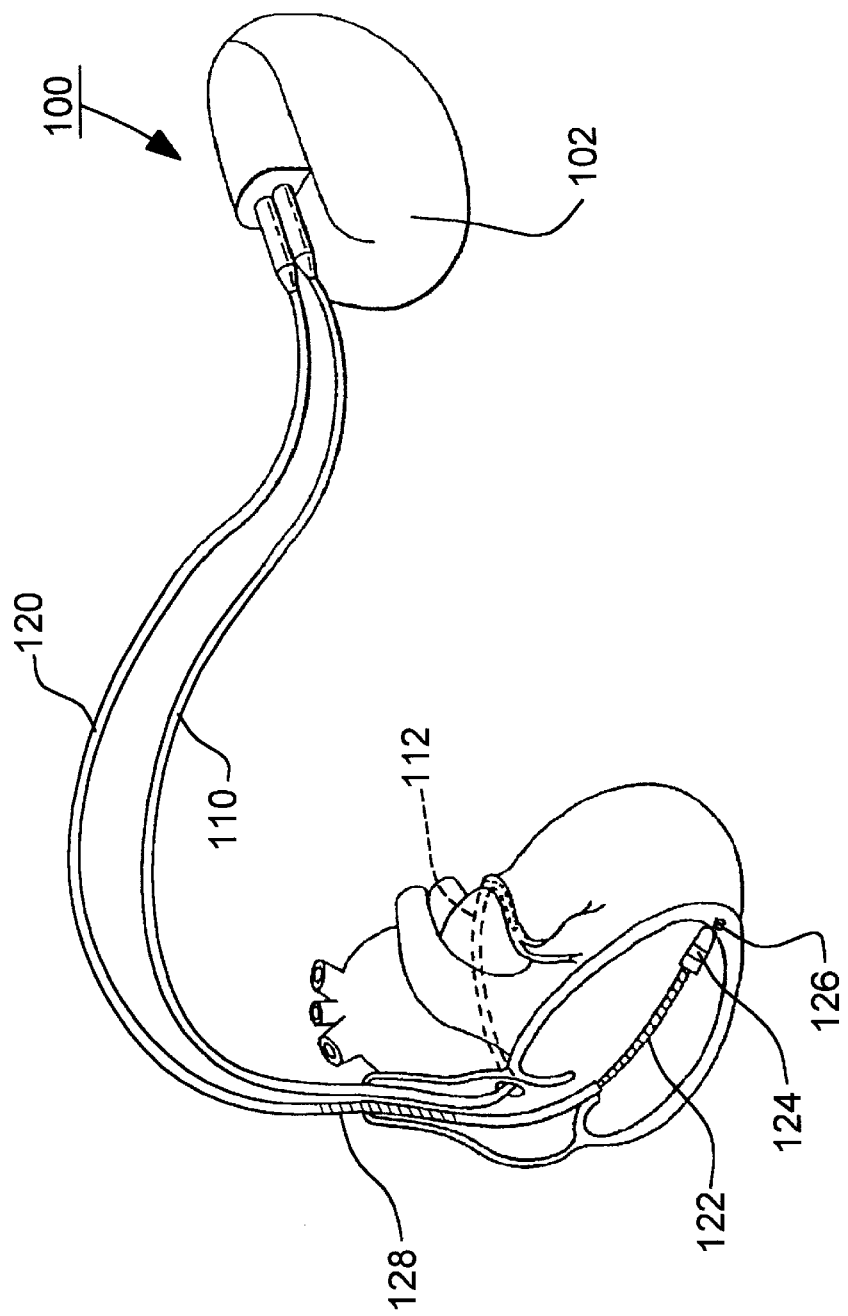
FIG. 1 illustrates a transvenous/subcutaneous electrode system in conjunction with a pacemaker/cardioverter/defibrillator embodying the present invention.

FIG. 1 illustrates an implantable pacemaker/cardioverter/defibrillator 100 and its associated lead system, as implanted in and adjacent to the heart. As illustrated, the lead system comprises a coronary sinus lead 110, a right ventricular lead 120, and a subcutaneous lead (not shown). The coronary sinus lead is provided with an elongated electrode located in the coronary sinus and great vein region at 112, extending around the heart until approximately the point at which the great vein turns downward toward the apex of the heart. The right ventricular lead 120 includes two elongated defibrillation electrodes 122 and 128, a ring electrode 124, and helical electrode 126, which is screwed into the tissue of the right ventricle at the right ventricular apex. The housing 102 of defibrillator 100 may serve as an additional electrode.

In conjunction with the present invention, the lead system illustrated provides electrodes that may be used to detect electrical activity in the ventricles, For example, ring electrode 124 and tip electrode 126 may be used to detect the occurrence of an R-wave and ring electrode 124 and subcutaneous defibrillation electrode (not shown) may be used to provide an EGM signal stored in response to R-wave detect. Alternatively, electrodes 124 and 126 may be used for both R-wave detection and as a source for the stored digitized EGM signal used for morphology analysis. Other electrode configurations may also be employed. In alternative embodiments in which atrial depolarizations are of interest, sensing electrodes would correspondingly be placed in or adjacent the patients atria.

Figure 2:
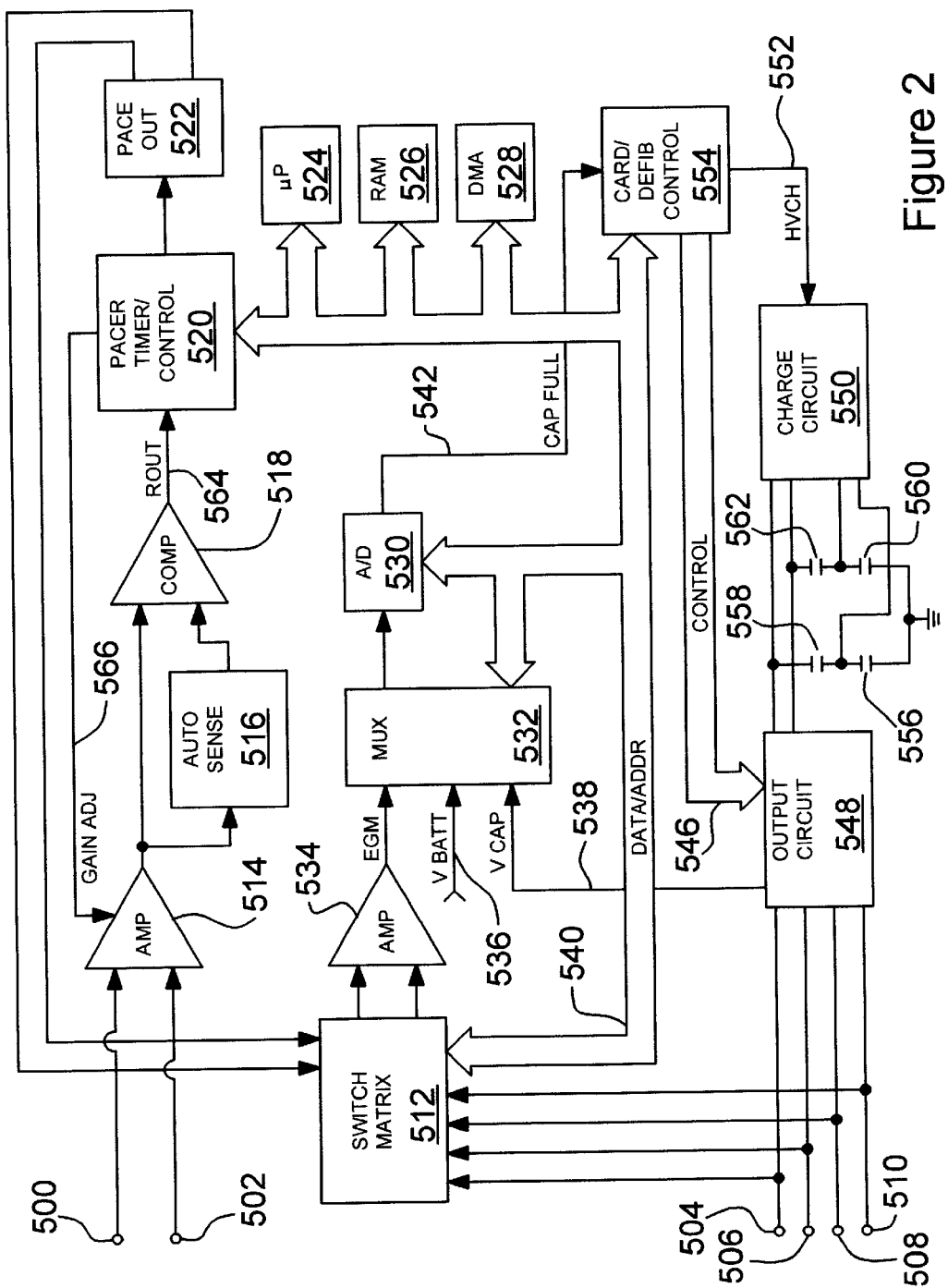
FIG. 2 is a schematic block diagram illustrating the structure of one embodiment of an implantable pacemaker/cardioverter/defibrillator in which the present invention may be embodied.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/defibrillator/cardioverters presently being implanted for clinical evaluation in the United States. The invention is also believed practicable in conjunction with implantable pacemaker/cardioverters/defibrillators as disclosed in prior U.S. Pat. No. 4,548,209, issued to Wielders, et al. on Oct. 22, 1985, U.S. Pat. No. 4,693,253, issued to Adams et al. on Sep. 15, 1987, U.S. Pat. No. 4,830,006, issued to Haluska et al. on May 6, 1989 and U.S. Pat. No. 4,949,730, issued to Pless et al. on Aug. 21, 1990, all of which are incorporated herein by reference in their entireties.

The device is illustrated as being provided with six electrodes, 500, 502, 504, 506, 508 and 510. Electrodes 500 and 502 may be a pair of electrodes located in the ventricle, for example, corresponding to electrodes 124 and 126 in FIG. 1. Electrode 504 may correspond to a remote, electrode located on the housing of the implantable pacemaker/cardioverter/defibrillator. Electrodes 506, 508 and 510 may correspond to the large surface area defibrillation electrodes located on the ventricular and coronary sinus leads illustrated in FIG. 1 or to epicardial or subcutaneous defibrillation electrodes.

Electrodes 500 and 502 are shown as hard-wired to the R-wave detector circuit; comprising bandpass amplifier 514, auto-threshold circuit 516 for providing an adjustable sensing threshold as a function of the measured R-wave amplitude and comparator 518. A signal is generated on R-out line 564 whenever the signal sensed between electrodes 500 and 502 exceeds the present sensing threshold defined by auto threshold circuit 516. As illustrated, the gain on the band pass amplifier 514 is also adjustable by means of a signal from the pacer timing and control circuitry 520 on GAIN ADJ line 566.

The operation of this R-wave detection circuitry may correspond to that disclosed in U.S. Pat. No. 5,117,824 by Keimel, et al., issued Jun. 2, 1992, incorporated herein by reference in its entirety. However, alternative R-wave detection circuitry such as that illustrated in U.S. Pat. No. 4,819,643, issued to Menken on Apr. 11, 1989 and U.S. Pat. No. 4,880,004, issued to Baker et al. on Nov. 14, 1989, both incorporated herein by reference in their entireties, may also usefully be employed to practice the present invention.

The threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article, "Reliable R-Wave Detection from Ambulatory Subjects", by Thakor et al., published in Biomedical Science Instrumentation, Vol. 4, pp 67–72, 1978, incorporated herein by reference in its entirety. An improved version of such an amplifier is disclosed in U.S. patent application Ser. No. 09/250,065, filed Feb. 12, 1999 by Rajasekhar, et al., for an "Implantable Device with Automatoic Sensing Adjustment", also incorporated herein by reference in its entirety. The invention may also be practiced in conjunction with more traditional R-wave sensors of the type comprising a band pass amplifier and a comparator circuit to determine when the band-passed signal exceeds a predetermined, fixed sensing threshold.

Switch matrix 512 is used to select which of the available electrodes make up the second electrode pair for use in conjunction with the present invention. The second electrode pair may comprise electrode 502 or 500 in conjunction with electrode 504, 506, 508 or 510, or may comprise other combinations of the illustrated electrodes, including combinations of the large surface defibrillation electrodes 506, 508, 510. Selection of which two electrodes are employed as the second electrode pair in conjunction with R-wave width measurement function is controlled by the microprocessor 524 via data/address bus 540. Signals from the selected electrodes are passed through band-pass amplifier 534 and into multiplexer 532, where they are converted to mult-bit digital signals by AID converter 530, for storage in random access memory 526 under control of direct memory address circuit 528. Microprocessor 524 employs the digitized EGM signal stored in random access memory 526 in conjunction with the morphology analysis method of the present invention For example, the microprocessor 524 may analyze the EGM stored in an interval extending from 100 milliseconds previous to the occurrence of an R-wave detect signal on line 564, until 100 milliseconds following the occurrence of the R-wave detect signal. The operation of the microprocessor 524 in performing the discrimination methods of the present invention is controlled by means of software stored in ROM, associated with microprocessor 524.

The remainder of the circuitry is dedicated to the provision of cardiac pacing, cardioversion and defibrillation therapies. The pacer timing/control circuitry 520 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 524, and are communicated to the pacing circuitry 520 via address/data bus 540. Pacer timing/control circuitry also determines the amplitude of the cardiac pacing pulses and the gain of band-pass amplifier, under control of microprocessor 524.

During VVI mode pacing, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502. The escape interval counter is also reset on generation of a pacing pulse, and thereby controls the basic timing of cardiac pacing functions, including anti-tachycardia pacing. The duration of the interval defined by the escape interval timer is determined by microprocessor 524, via data/address bus 540. The value of the count present in the escape interval counter when reset by sensed R-waves may be used to measure the duration of R—R intervals, to detect the presence of tachycardia and to determine whether the minimum rate criteria are met for activation of the width measurement function.

Microprocessor 524 operates as an interrupt driven device, under control of software stored in the ROM associated with microprocessor 524 and responds to interrupts from pacer timing/control circuitry 520 corresponding to the occurrence of sensed R-waves and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts. These calculations include those described in more detail below associated with the discrimination methods of the present invention.

In the event that a tachycardia is detected, and an anti-tachycardia pacing regimen is desired, appropriate timing intervals for controlling generation of antitachycardia pacing therapies are loaded from microprocessor 524 into the pacer timing and control circuitry 520, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 524 employs the counters to in timing and control circuitry 520 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. Thereafter, delivery of the timing of the defibrillation or cardioversion pulse is controlled by pacer timing/control circuitry 520. One embodiment of an appropriate System for delivery and synchronization of cardioversion and defibrillation pulses, and controlling the timing functions related to them is disclosed in more detail in U.S. Pat. No. 5,188,105, issued to Keimel on Feb. 23, 1993 and incorporated herein by reference in its entirety. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed. Similarly, known circuitry for controlling the timing and generation of antitachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al. on May 13, 1986, all of which are incorporated herein by reference in their entireties may also be used.

In modern pacemaker/cardioverter/defibrillators, the particular antitachycardia and defibrillation therapies are programmed into the device ahead of time by the physician, and a menu of therapies is typically provided. For example, on initial detection of tachycardia, an anti-tachycardia pacing therapy may be selected. On redetection of tachycardia, a more aggressive anti-tachycardia pacing therapy may be scheduled. If repeated attempts at anti-tachycardia pacing therapies fail, a higher-level cardioversion pulse therapy may be selected thereafter. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al. The present invention is believed practicable in conjunction with any of the known anti-tachycardia pacing and cardioversion therapies, and it is believed most likely that the invention of the present application will be practiced in conjunction with a device in which the choice and order of delivered therapies is programmable by the physician, as in current implantable pacemaker/cardioverter/defibrillators.

In the present invention, selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multielectrode, simultaneous pulse regimen or a multielectrode sequential pulse regimen. Monophasic or biphasic pulses may be generated. One example of circuitry which may be used to perform this function is set forth in U.S. Pat. No. 5,163,427, issued to Keimel on Nov. 17, 1992, incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in the context of the present invention. Alternatively single monophasic pulse regimens employing only a single electrode pair according to any of the above-cited references that disclose implantable cardioverters or defibrillators may also be used.

As discussed above, switch matrix 512 selects which of the various electrodes are coupled to band pass amplifier 534. Amplifier 534 may be a band- pass amplifier, having a band pass extending for approximately 0.5 to 200 hertz. The filtered EGM signal from amplifier 534 is passed through multiplexer 532, and digitized in A-D converter circuitry 530. The digitized EGM data is stored in random access memory 526 under control of direct memory address circuitry 528. Preferably, a portion of random access memory 526 is configured as a looping or buffer memory, which stores at least the preceding several seconds of the EGM signal.

The occurrence of an R-wave detect signal on line 564 is communicated to microprocessor 524 via data/address bus 540, and microprocessor 524 notes the time of its occurrence. If the morphology analysis function is activated, microprocessor 524 may, for example, wait 100 milliseconds or other physician selected interval following the occurrence of the R-wave detect signal, and thereafter transfer the most recent 200 milliseconds or other physician selected interval of digitized EGM stored in the looping or buffer memory portion of the random access memory circuit 526 to a second memory location, where the contents may be digitally analyzed according to the present invention. In this case, the transferred 200 milliseconds of stored EGM will correspond to a time window extending 100 milliseconds on either side of the R-wave detect signal. Window sizes in any case should be sufficient to allow analysis of the entire QRS complexes associated with the detected R-waves. The microprocessor also updates software-defined counters that hold information regarding the R—R intervals previously sensed. The counters are incremented on the occurrence of a measured R—R intervals falling within associated rate ranges. These rate ranges may be defined by the programming stored in the RAM 526.

The following exemplary VT/VF detection method corresponds to that employed in commercially marketed Medtronic implantable pacemaker/cardioverter/ defibrillators and employs rate/interval based timing criteria as a basic mechanism for detecting the presence of a tachyarrhythmia. To this end, the device defines a set of rate ranges and associated software-defined counters to track the numbers of intervals falling within the defined ranges.

A first rate range may define a minimum R—R interval used for fibrillation detection, referred to as "FDI". The associated VF count preferably indicates how many of a first predetermined number of the preceding R—R intervals were less than FDI.

A second rate range may include R—R intervals less than a lower tachycardia interval "TDI", and the associated VT count (VTEC) is incremented in response to an R—R interval less than TDI but greater then FDI, is not affected by R—R intervals less than FDI, and is reset in response to R—R intervals greater than TDI.

Optionally, the device may include a third rate range including R—R intervals greater than the FDI interval, but less than a fast tachycardia interval (FTDI) which is intermediate the lower tachycardia interval (TDI) and the lower fibrillation interval (FDI). In devices that employ this optional third rate range, it is suggested that the width criterion be employed only in conjunction with detection of rhythms within the lower rate range, e.g., sequences of intervals between TDI and FTDI.

For purposes of the present example, the counts may be used to signal detection of an associated arrhythmia (ventricular fibrillation, fast ventricular tachycardia or lower rate ventricular tachycardia) when they individually or in combination reach a predetermined value, referred to herein as "NID's" (number of intervals required for detection). Each rate zone may have its own defined count and NID, for example "VFNID" for fibrillation detection and "VTNID" for ventricular tachycardia detection or combined counts may be employed. These counts, along with other stored information reflective of the previous series of R—R intervals such as information regarding the rapidity of onset of the detected short R—R intervals, the stability of the detected R—R intervals, the duration of continued detection of short R—R intervals, the average R—R interval duration and information derived from analysis of stored EMG segments are used to determine whether tachyarrhythmias are present and to distinguish between different types of tachyarrhythmias.

For purposes of illustrating the invention, an exemplary rate/interval based ventricular tachyarrhythmia detection method is described above. Other tachyarrhythmia detection methodologies, including detection methods as described in U.S. Pat. No. 5,991,656, issued to Olson, et al. on Nov. 23, 1999, U.S. Pat. No. 5,755,736, issued to Gillberg, et al. on May 26, 1998, both incorporated herein by reference in their entireties, or other known ventricular and/or atrial tachyarrhythmia detection methods may be substituted. It is believed that the discrimination methods of the present invention may be usefully practiced in conjunction with virtually any underlying atrial or ventricular tachyarrhythmia detection scheme. Other exemplary detection schemes s are described in U.S. Pat. No. 4,726,380, issued to Vollmann, U.S. Pat. No. 4,880,005, issued to Pless et al. and U.S. Pat. No. 4,830,006, issued to Haluska et al., incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology,* Oct. 7–10, 1986, IEEE Computer Society Press, pages 167–170, also incorporated by reference in its entirety herein. However, other criteria may also be measured and employed in conjunction with the present invention.

For purposes of the present invention, the particular details of implementation of the rate/interval based detection methodologies are not of primary importance. However, it is required that the rate based detection methodologies employed by the device allow identification and detection of rhythms in the rate range in which operation of the morphology analysis function is desired. It is also important that the morphology analysis function be initiated far enough in advance of the point at a heart rhythm within the desired rate range can be detected to allow for analysis of the required number of waveforms before the heart rhythm is diagnosed positively as being within the desired rate range. In this fashion, the results of the morphology analysis will be available for use immediately in response to the rate or interval based criteria being met. Diagnosis of the detected arrhythmia and a selection of the therapy to be delivered can likewise be done immediately in response to the rate or interval based criteria being met.

For example, the morphology analysis function in conjunction with the above-described detection scheme may be continuously activated or may appropriately be initiated and analysis of R-wave morphologies begun at the time the VT count (VTEC) equals VTNID, minus "n", where "n" is the number of R-waves employed to determine whether the morphology based criterion is met. The same result may also be accomplished by initiating morphology analysis of in response to the VT count reaching a different predetermined value substantially less than VTNID.

Figure 3A:
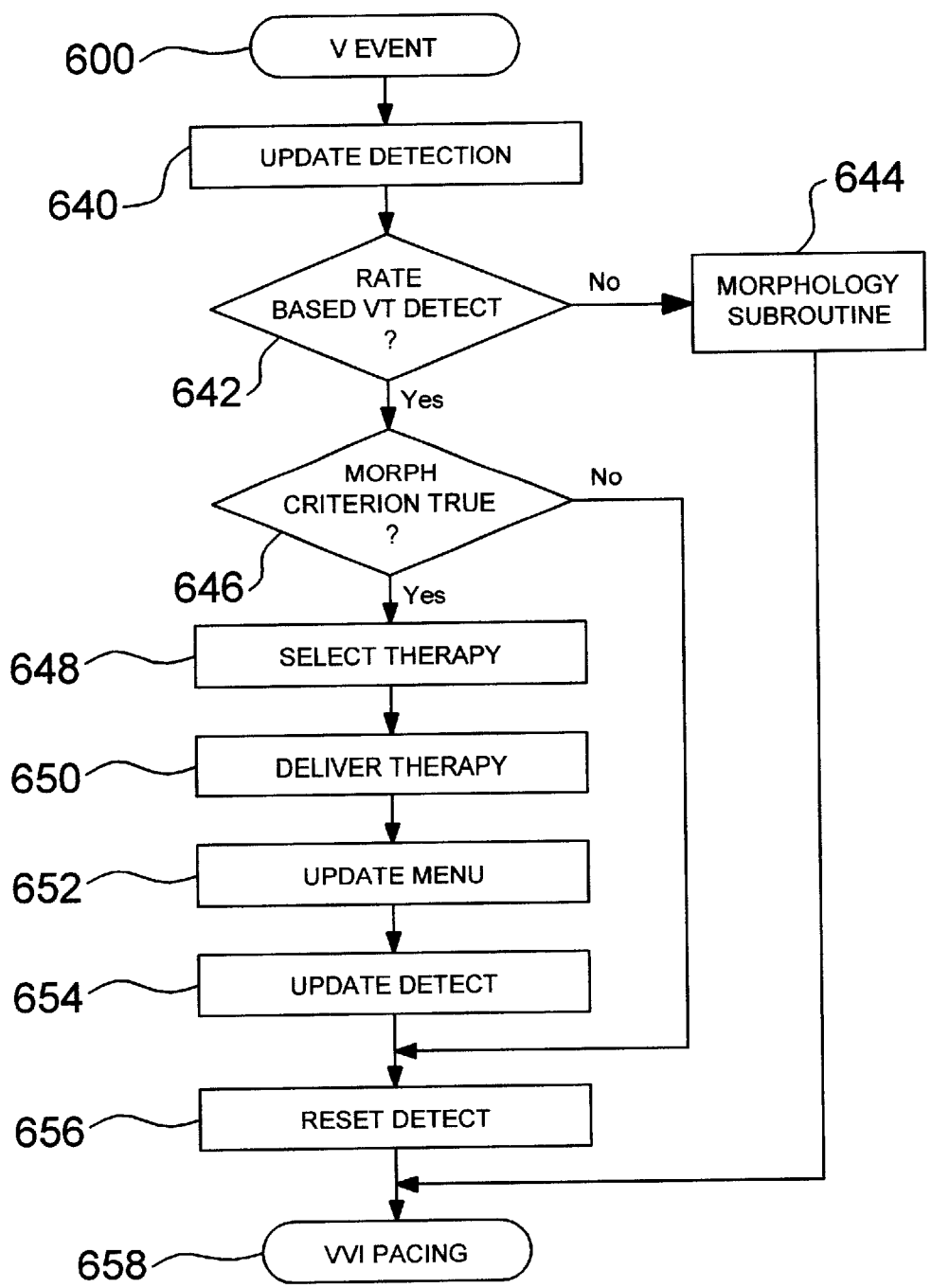
FIGS. 3A and 3B are functional flow charts illustrating the over-all operation of tachyarrhythmia detection functions and their interrelation with the morphology analysis function provided by the present invention, as embodied in a microprocessor based device as illustrated in FIG. 2.

FIG. 3A is a flow chart representing a first example of the operation of the device illustrated in FIG. 2, in conjunction with the morphology analysis function provided by the present invention. FIG. 3A is intended to functionally represent that portion of the software employed by microprocessor 524 (FIG. 3) which implements the morphology function and which employs the morphology analysis in conjunction with VT detection. This portion of the software is executed in response the sensing of a ventricular depolarization at 600. At 640 the rate/interval based detection criteria are updated at 640, for example by incrementing VTEC, as discussed above.

In the event that the rate/interval-based criteria for tachycardia detection are not met at 642, the morphology analysis subroutine is performed at 644. This subroutine is described in detail in conjunction with FIGS. 4, et seq. For purposes of FIG. 3A, it is only important to understand that the morphology analysis subroutine determines whether the morphology of at least a predetermined number of the preceding series of R waves is indicative of a ventricular tachycardia. If so, the morphology criterion is met. Meeting the morphology criteria is a prerequisite in the flow chart of FIG. 3 to delivery of a ventricular anti-tachycardia therapy.

In the event that the morphology criterion is met at 646, the therapy menu is examined at 648 to determine the presently scheduled anti-tachycardia therapy. The scheduled therapy is delivered at 650, the tachycardia menu is updated at 652 to reflect the delivery of the therapy at 650, and the detection criteria are updated at 654 to reflect the fact that a tachycardia has previously been detected and not yet terminated. Detection criteria are reset at 656, and the device returns to bradycardia pacing until redetection tachycardia or fibrillation or detection of termination of tachycardia. Detection of termination of tachycardia may be accomplished by means of detection of a predetermined number of sequential R—R intervals indicative of normal heart rate. Normal heart rate may be defined as R—R intervals greater than TDI.

Figure 3B:
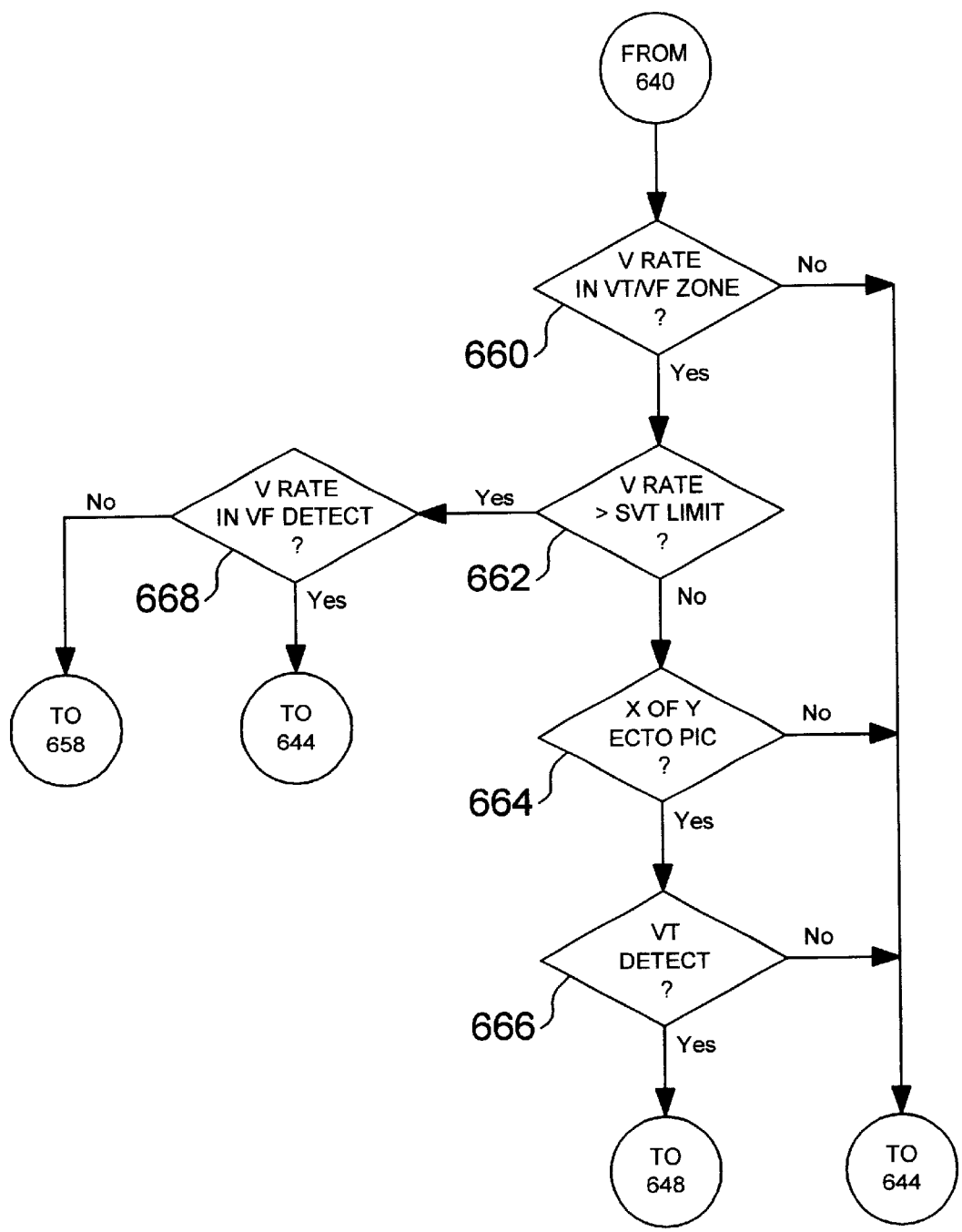

FIG. 3B illustrates an alternative example of the integration of the morphology analysis function provided by the present invention with rate-based detection criteria. The illustrated functions should be understood to be substituted for elements 642 and 646 of FIG. 3A. In this embodiment after updating the various counts, etc associated with rate based detection, the microprocessor first checks at 660 to determine whether, based upon prior stored V—V interval durations, the patient's present ventricular rate is indicative of a ventricular tachyarrhythmia, e.g. faster than the rate corresponding to the maximum interval for VT detection, as discussed above. If not, the device continues accumulate information on the morphology of the R-waves at 644. If the ventricular rate is at least fast enough to be considered a VT, the microprocessor determines at 662 whether the rate is fast enough to qualify as a fast VT, e.g. e.g. faster than the rate corresponding to the maximum interval for VT detection, as discussed above. If not, indicating that a slow VT is likely present, the microprocessor checks at 664 to see whether a predetermined percentage (e.g. 6 of 8) of the preceding R-waves have been classified as abnormal. If so, the microprocessor checks at 666 to determine whether the rate-based criteria for VT detection have been met. If so, an appropriate therapy is delivered at 648. If the rate based VT detection criteria are not met at 666, the device continues accumulate information on the morphology of the R-waves at 644. Unlike the example of FIG. 3A, meeting the rate based VT detection criteria without meeting the morphology criteria does not result in a reset of the rate based detection criteria.

In the event that the rate is rapid enough to be considered a fast VT or VF at 662, the microprocessor determines at 668 whether the rate based detection criteria for these arrhythmias have been met. If so, an appropriate therapy is delivered at 648. Otherwise, the device continues accumulate information on the morphology of the R-waves at 644.

Wavelet-Based EGM Morphology Discrimination

The EGM width discrimination method as described in U.S. Pat. No. 5,312,441 issued to Mader, et al. utilizes a single characteristic of EGM morphology (the width of the R-wave) to discriminate SVT from VT. The present invention provides a new EGM discrimination method that utilizes a signal processing method called the "wavelet-transform" to describe multiple characteristics of EGM morphology to better discriminate SVTs and VTs. The method of the present invention is fundamentally based on "template matching", a mathematical comparison of a known template EGM (SVT or normal sinus rhythm) to the EGMs from an unknown rhythm in order to classify the rhythm based on EGM morphology. Some background on the wavelet transform and how it is used to describe EGM morphology follows and a more detailed description of the wavelet-based EGM morphology discrimination algorithm is set forth below.

Wavelets have theoretical foundations dating back to 1910, but it was only recently (mid 1980's) that a unifying theory of wavelets has developed in the area of applied mathematics and signal processing. The Wavelet transform is a mathematical technique that expands signals onto basis functions ("wavelets") that are defined by time-scaling (or "stretching" in the time domain) and time-shifting a single prototype function or "mother wavelet". This method of analyzing signals can be thought of as a "mathematical microscope", where various degrees of focus are created by the various time-scaling factors of the mother wavelet. Time resolution is maintained by choosing a mother wavelet function that has finite (short) duration and through shifting this function to cover the duration of the signal being analyzed. The wavelet transform is often explained as a mechanism for providing higher time and frequency resolution than the more commonly known Fourier transform technique, which expands signals onto sine and cosine waves (orthogonal basis functions) to accurately describe the frequency content of the signal with very limited time resolution. Unlike the Fourier method, there are many possible basis functions that may be used in performing wavelet analysis.

Haar Wavelet Transform

The Haar wavelet transform is employed by the preferred embodiments of the present invention, as the computation of the Haar wavelet transform as implemented substantially simplifies the processing to be performed by an implanted device embodying the invention.

The Haar function was first described by a German mathematician, A. Haar, in 1910. The Haar function is defined as set forth below. This function forms a very simple orthonormal wavelet basis, and can be used to define a Discrete Wavelet Transform (DWT). The Mother wavelet of the Haar transform is defined as follows:

$\psi(x)=1$ if $0 \le x<0.5$; $-1$ if $0.5 \le x<1$; 0 otherwise

The DWT of a signal with N samples results in N wavelet coefficients that represent the expansion of the signal into different wavelets formed by time-scaling, time-shifting, and amplitude scaling the mother wavelet function (the DWT is analogous to the N sample discrete Fourier transform that results in N Fourier coefficients representing the expansion of the signal into frequencies of various amplitudes and phase). The inverse DWT of the waveform's wavelet coefficients will result in a complete reconstruction of the original waveform.

The DWT of a signal f(t), is represented by the following equation:

$$f(t) = \sum_{j,k} a_{j,k} \psi_{j,k}(t)$$

where:

f(t) is any finite energy, real input signal;

j are the time-shift indices;

k are the time-scaling indices;

$a_{j,k}$ are the wavelet coefficients; and $\psi_{j,k}(t)$ are the wavelets.

The equation above is useful to illustrate that the DWT is computed using a pre-defined set of wavelets, $\psi_{j,k}(t)$ which are time-shifted and time-scaled versions of the mother wavelet $\psi(t)$. In addition, each time-scale and time-shift has a corresponding wavelet coefficient (i.e. amplitude factor) $a_{j,k}$. The number of time-scaling and time-shifting factors applied to the mother wavelet are predefined by the computational structure of the DWT, which is commonly based on dyadic (or factors of 2) sampling of the time-scaling and time-shifting functions used to define the continuous wavelet transform. This means that the wavelets $\psi_{j,k}(t)$ are independent of the function f(t), and thus for a fixed number of samples and mother wavelet function the DWT is uniquely described by the wavelet coefficients $a_{j,k}$.

Figure 4:
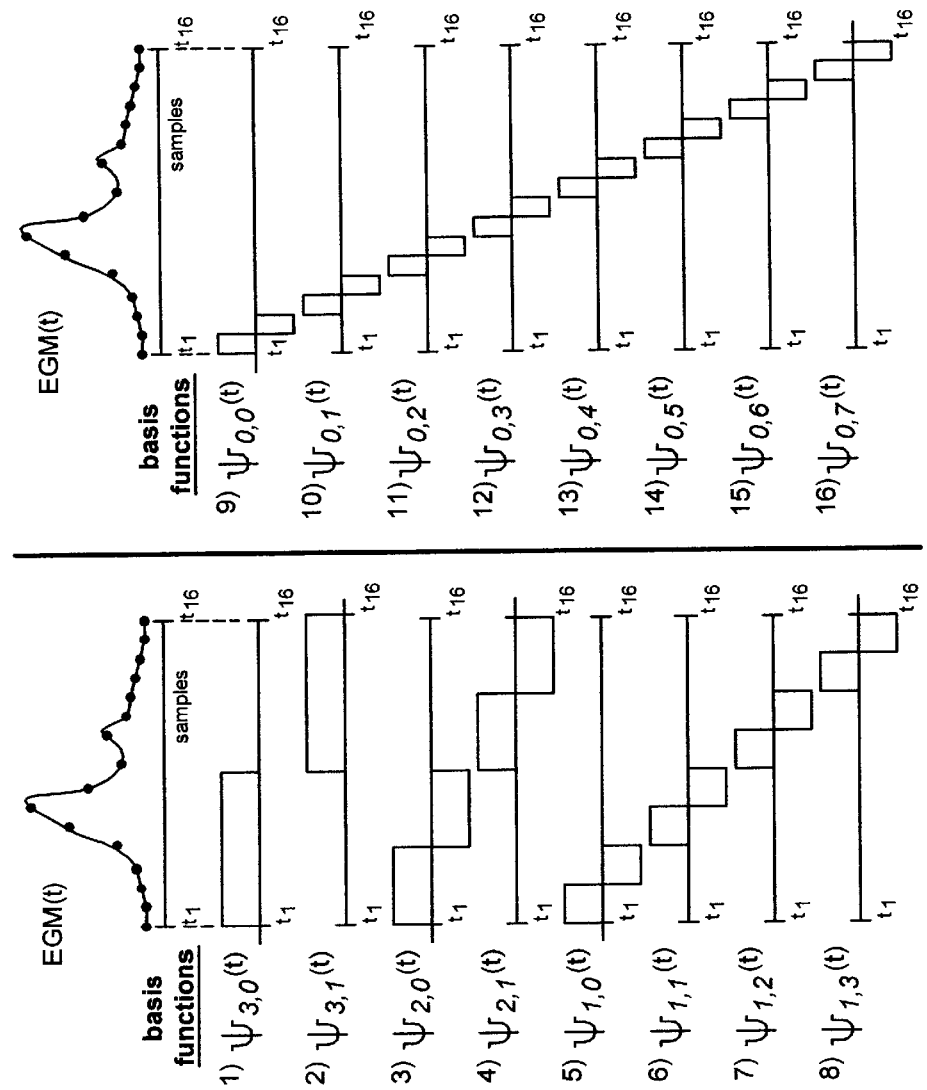
FIG. 4 is an illustration of the wavelet structure of an exemplary Haar wavelet transform as employed by the preferred embodiments of the present invention.

It is useful to consider an example of the DWT in order to illustrate the properties of multi-resolution signal decomposition. Consider the case of an input signal f(t) with 16 samples $\{f(t_1), f(t_2), \ldots f(t_{16})\}$. FIG. 4 shows the dyadic structure of the DWT of f(t) and illustrates that the resulting 16 wavelets arise from 4 different time-scaling factors (the k indices) applied to the mother wavelet, and each resulting time-scaled wavelet has either 2, 4 or 8 time-shift factors (the j indices). The structure of the DWT and the definition of the wavelets is independent of the f(t), and thus only the wavelet coefficients, $a_{j,k}$ will change when f(t) changes. Because the definition of the wavelets is fixed for a fixed length DWT, It is useful to use the shorthand notation of wavelet coefficient number, $c_i$, as a way of referring simultaneously to wavelet coefficients $a_{j,k}$ and associated wavelets $\psi_{j,k}(t)$.

FIG. 4 shows the 16 wavelets, $\psi_{j,k}(t)$, used to expand a 16 sample signal when the Haar function is used for the mother wavelet DWT. Amplitude information (the wavelet coefficients $a_{j,k}$ are intentionally left out of FIG. 4 in order to illustrate the notion of the time-scaling and time-shifting factors applied to the mother Haar wavelet to form the DWT. The mother wavelet is generally defined to be the narrowest function, in FIG. 4 this corresponds to the shape of wavelets 9–16. As can be seen in FIG. 4, wavelets 9–16 are different time shifts of the same function.

The four fundamental wavelet shapes each correspond to a different timescale factor (expansion) of the mother wavelet. Since the signal f(t) is represented by several different time-scaled versions of the same function, the wavelet transform is often referred to as multi-resolution signal decomposition since it expands the signal into functions with various resolutions (wide wavelets are low resolution, narrow wavelets are high resolution). The number of time-shifts for each of the 4 time-scales is determined by the number of non-overlapping windows needed to cover all 16 samples of f(t). The time-scaled version of the mother wavelets that is 8 samples wide has 2 shifts, the time-scaled version of the mother wavelet that is 4 samples wide has 4 shifts, and the time-scaled version of the mother wavelet that is 2 samples wide has 8 shifts.

The dyadic structure of the DWT is easily extended to describe wavelets for f(t)s with more (or fewer) samples, as long as the number of samples is a power of 2. For example, for a function with 64 points, the highest resolution (or narrowest) wavelet will have identical shape and width to the highest resolution wavelet in FIG. 5 (wavelets 9–16 have a width of 2 samples). However, for a 64 point function, a wavelet with a width of 2 must be shifted to 32 non-overlapping windows in order to cover the entire 64 point function. The widest wavelet in a 64 point Haar DWT will have a width that spans 32 samples. For f(t) with 2N samples, the number different wavelet scales will be N. Note that for a function of length $2^4=16$, there are 4 different wavelet scales, and for a function of length $2^6=64$, there will be 6 different scales. The wavelets of each different scale will be twice as wide as the next widest wavelet, and will be time-shifted with the proper number of non-overlapping shifts to span the total number of samples in f(t).

The Haar wavelet transform can also be computed to weight the contributions of certain time-scales to emphasize their contributions. This is important for additional simplification of the computations required as well as altering the discrimination performance of the algorithm. With emphasis or weighting applied to the wider scale wavelet transform coefficients relative to the narrow scale coefficients, the contribution of noise and insignificant EGM wave shape information is reduced in the resulting wavelet transform. As described in "A Primer on Wavelets and their Scientific Applications" by Walker, Chapman and Hall/CRC, 1999 pages 1–9, incorporated herein by reference in its entirety, the Haar wavelet transform as typically performed requires multiple divisions by the division by the square root of two in order to derive the wavelet coefficients. As discussed in Walker, These division steps are necessary to preserve the accuracy of the waveform. However, eliminating this division operation greatly simplifies computations and emphasizes the wider Haar transform coefficients. Replacing divisions by the square root of two with divisions by two greatly simplifies computations since division by two can be done by a bit shift in the microprocessor and also has the result of approximating the results of the divisions by two in the textbook Haar transform definition. In the preferred embodiment of the invention described below, the Haar wavelet transform is scaled by simply eliminating all divisions by square root of two (i.e. leaving all terms normally divided by the square root of two un-altered), thus providing additional emphasis of the wider wavelet transform coefficients. However, other applications of this method may use different scaling factors to provide improved performance. The DWT may also be computed for data lengths that are not a power of 2.

In one preferred embodiment of this invention, a 48 point Haar wavelet transform weighted to emphasize the wider transform coefficients is computed as follows, where A[n] represents the amplitude of a sample data point. The convention for numbering the wavelet coefficients is reversed from that described above in conjunction with FIG. 4, with the widest coefficients having the highest numbers. Either numbering convention may be employed.

$c[0]=a[0]-a[1]$ $c[1]=a[2]-a[3]$ $c[2]=a[4]-a[5]$

. . .

$c[23]=a[46]-a[47]$ $c[24]=a[0]+a[1]-a[2]-a[3]$ $c[25]=a[4]+a[5]-a[6]-a[7]$ $c[26]=a[8]+a[9]-a[10]-a[11]$

. . .

$c[35]=a[44]+a[45]-a[46]-a[47]$ $c[36]=a[0]+a[1]+a[2]+a[3]-a[4]-a[5]-a[6]-a[7]$ $c[37]=a[8]+a[9]+a[10]+a[11]-a[12]-a[13]-a[14]-a[15]$ $c[38]=a[16]+a[17]+a[18]+a[19]-a[20]-a[21]-a[22]-a[23]$ $c[39]=a[24]+a[25]+a[26]+a[27]-a[28]-a[29]-a[30]-a[31]$ $c[40]=a[32]+a[33]+a[34]+a[35]-a[36]-a[37]-a[38]-a[39]$ $c[41]=a[40]+a[41]+a[42]+a[43]-a[44]-a[45]-a[46]-a[47]$ $c[42]=a[0]+a[1]+a[2]+a[3]+a[4]+a[5]+a[6]+a[7]-a[8]-a[9]-a[10]-a[11]-a[12]-a[13]-a[14]-a[15]$ $c[43]=a[16]+a[17]+a[18]+a[19]+a[20]+a[21]+a[22]+a[23]-a[24]-a[25]-a[26]-a[27]-a[28]-a[29]-a[30]-a[31]$ $c[44]=a[32]+a[33]+a[34]+a[35]+a[36]+a[37]+a[38]+a[39]-a[40]-a[41]-a[42]-a[43]-a[44]-a[45]-a[46]-a[47]$ $c[45]=a[0]+a[1]+a[2]+a[3]+a[4]+a[5]+a[6]+a[7]+a[8]+a[9]+a[10]+a[11]+a[12]+a[13]+a[14]+a[15]-a[16]-a[17]-a[18]-a[19]-a[20]-a[21]-a[22]-a[23]-a[24]-a[25]-a[26]-a[27]-a[28]-a[29]-a[30]-a[31]$ $c[46]=a[16]+a[17]+a[18]+a[19]+a[20]+a[21]+a[22]+a[23]+a[24]+a[25]+a[26]+a[27]+a[28]+$ $a[29]+a[30]+a[31]-a[32]-a[33]-a[34]-a[35]-a[36]-a[37]-a[38]-a[39]-a[40]-a[41]-a[42]-a[43]-a[44]-a[45]-a[46]-a[47]$

In addition to filtering based on the amplitude of the wavelet coefficients as described above, it may be desired to instead or in addition filter out wavelet coefficients representing certain scales where unimportant signal information is represented. For example, the wavelet coefficients representing the widest wavelets may be set to zero to eliminate the contributions of the widest scale attributes of the signal. Other sets of wavelet coefficients representing a particular scale may be zeroed out to eliminate the contributions, depending on the application desired. In the 48 point Haar wavelet transform described above, for example, the last 3 wavelet coefficients which correspond to the widest wavelets and which do not provide significant signal discrimination may be set to 0 and thereby filtered out. Alternatives to this method may utilize all wavelet coefficients, or may filter out different sets corresponding to different scales in order to optimize discrimination performance.

As mentioned previously, the DWT can be defined using other wavelet functions. In many instances, the wavelet functions are chosen to be non-zero for some finite duration in order to maintain the time-localization property of the DWT. Additional constraints on the shape of the wavelet functions are generally used so that good frequency resolution can be achieved, especially when the DWT is used for time-frequency signal analysis. Compared to other wavelet functions, the Haar function does not provide very good time-frequency localization. However, as will be shown in below, the Haar wavelet does have the ability to localize salient time-domain features of EGM waveforms for purposes of discriminating waveforms. For this application, the relatively poor frequency localization does not seem to affect discrimination performance.

Wavelet Based EGM Morphology Discrimination Algorithm—First Embodiment

The present invention provides new EGM morphology discrimination methods based on the Haar Discrete Wavelet Transform (DWT) described above. The goal of these new methods is to classify rhythms based on EGM waveform morphology. The specific application described herein is for discrimination of SVTs from VT/VF, so that inappropriate therapies can be averted. For example, ventricular therapies may be withheld for any rhythm with EGM waveform morphology that is classified to be SVT. However, the basic discrimination methods disclosed are believed applicable to other waveforms, for example atrial depolarization waveform as discussed above. In addition, while the embodiments described herein employ a normal waveform as the basis for the waveform template, alternative embodiments might employ a defined aberrant waveform as the basis for a template, e.g. a re-entrant ventricular tachycardia waveform. In such embodiments, a waveform that did not show sufficient similarity to the template might be result in the withholding of therapy, in an inverse manner to the enablement of therapy in response to occurrences of waveforms that do not correspond to the template in the embodiments disclosed herein. In addition, white the embodiments disclosed herein employ only a single template, alternative embodiments of the present invention may employ multiple templates, each indicative of an identified heart rhythm.

Since EGM waveforms vary for different people and electrodes from which they are recorded the disclosed embodiments of the methods of the present invention rely on establishing the specific EGM morphology or morphologies that should be considered "normal" for each patient. This can be done either automatically or with user supervision, and from a patient's normal sinus rhythm or stored episode data from spontaneous SVTs that resulted in inappropriate therapy. As in the EGM Width discrimination method described in the above-cited Mader, et al. patent, the wavelet-based EGM discrimination method of the present embodiments of the invention obtain EGM waveform snapshots derived from the incoming stream of real-time EGM data by centering a morphology window at each bipolar sensed event. This technique has been powerful for limiting EGM morphology to ventricular depolarizations, allowing the use of far-field EGMs for EGM morphology description, and reducing the influence of P-waves and T-waves in the morphological description of ventricular depolarizations.

Figure 5:
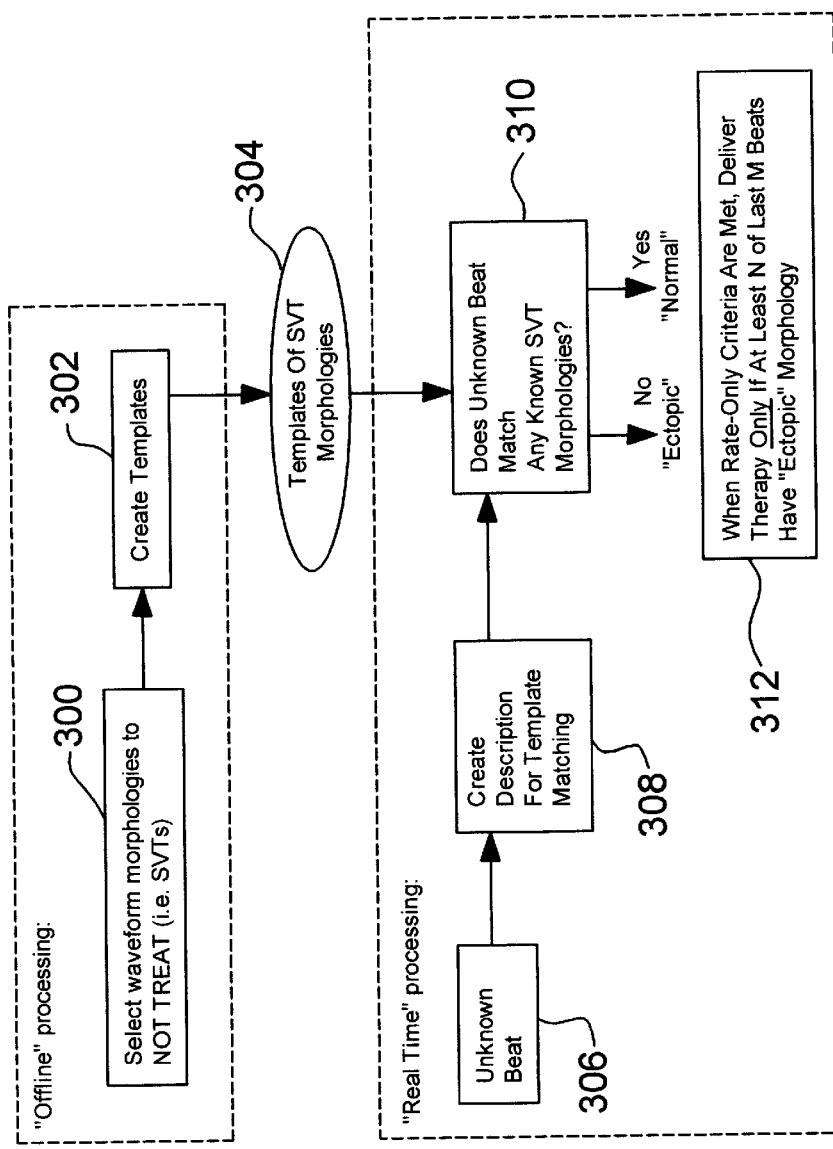
FIG. 5 is a functional diagram illustrating the wavelet based waveform discrimination methods of the present invention.

FIG. 5 presents a block diagram of the EGM morphology discrimination method according to the first embodiment of the present invention. The first step 300 of the method is to select the waveforms representing the EGM morphologies that should be considered normal to create templates. This step is done off-line (meaning not on every ventricular event) either via the programmer with user-supervision to verify the rhythm being used for the template(s) or during slow ventricular rates solely by the implanted device, or both. It is a much bigger job for the implanted device to automatically update templates because of the need to be certain that templates aren't generated from ectopic beats. Creating of templates at 302 involves computing the DWT coefficients from "normal" waveforms, extracting the wavelet coefficients that describe the salient features of the waveform to create the templates. The templates are then stored in the memory of the implanted device at 304. The remainder of the method must be processed in real-time, i.e. updated on each ventricular beat during a fast rhythm. During the fast rhythm, the "unknown" EGM waveforms from the ongoing rhythm are obtained at 306, processed by means of the above-described Haar wavelet transform at 308 and matched against the stored templates at 310. If the unknown waveform is a close match to one of the templates, the current beat is classified as NORMAL, otherwise the current beat is classified as ECTOPIC. If the waveforms are predominately ECTOPIC, then the rhythm is NOT an SVT, and ventricular therapies are delivered at 312 when the rate-based or other detection criteria are satisfied. The details of the method illustrated in FIG. 5 are discussed below.

As in other transform methods, the Haar wavelet transform results in a description of the input signal that has the same number of data points as the original signal, but is assembled from a different viewpoint or basis. The Discrete Wavelet Transform (DWT) describes the signal in terms of a basis that represents the features of the signal at different time-scales (i.e. resolutions). By sorting through and combining the wavelet coefficients $a_{j,k}$ (and associated wavelets $\psi_{j,k}(t)$) at each of the different resolutions, one can obtain representations of the signal at a high resolution using the narrowest wavelets and at a lower resolution with the widest wavelets. For data compression, a subset of wavelet coefficients at a variety of resolutions may be selected to represent the complete signal with fewer than the original number of points. This may be done by performing a DWT and selecting the wavelets with the largest contribution to the signal. This can be done easily by selecting the wavelet coefficients $a_{j,k}$ with the highest amplitude. The wavelet coefficients with the largest absolute amplitudes (and their associated wavelets) represent the largest contributions to the signal. In data compression, reconstruction of the signal with N data points using the M largest amplitude wavelet coefficients (and associated wavelets) yields a signal representation with a compression factor of N/M.

Figure 6:
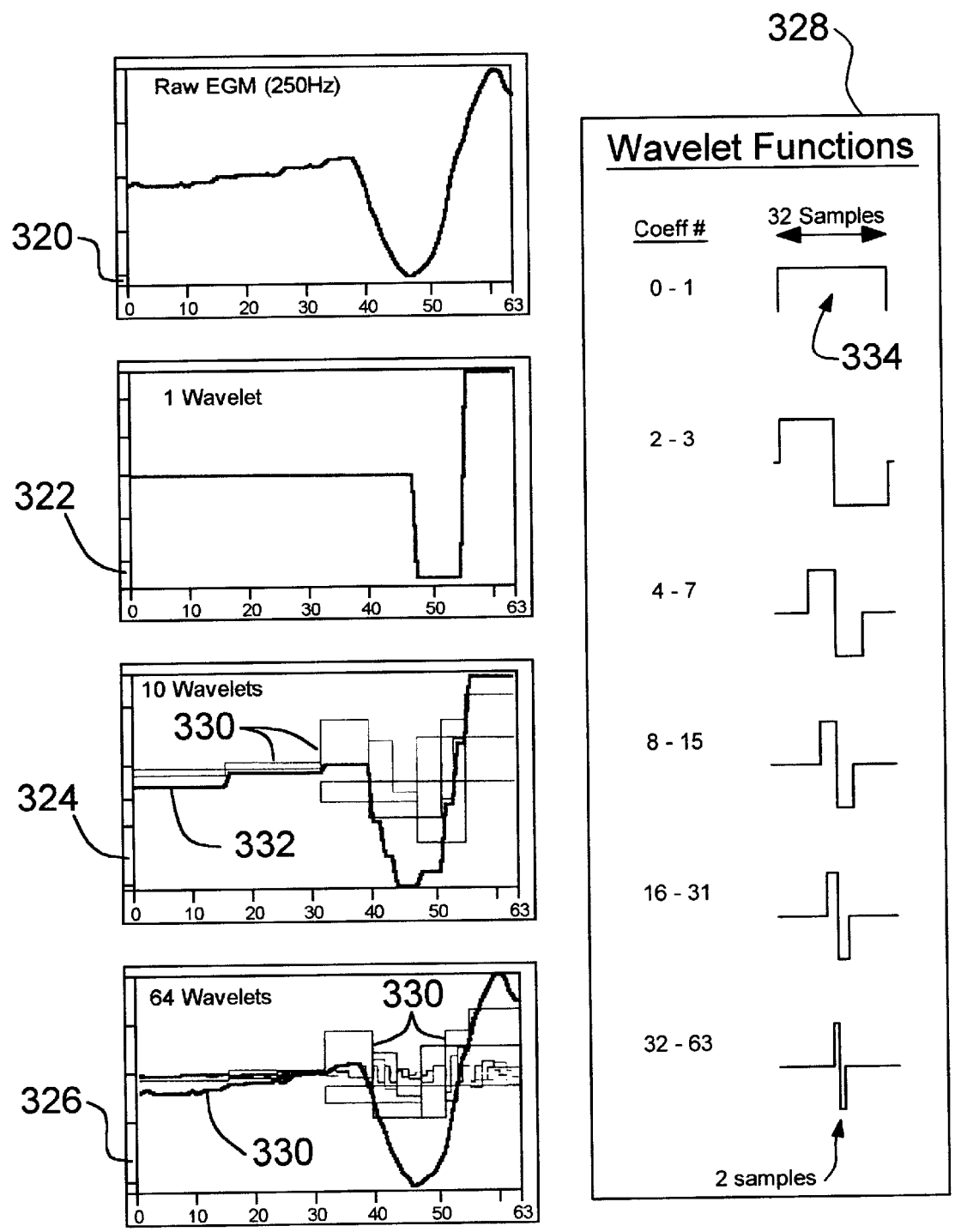
FIG. 6 is an illustration of the reconstruction of waveforms from wavelet coefficients obtained using the Haar wavelet transform of the present invention.

A 64 sample segment of EGM waveform (Raw EGM at a sampling rate of 250 Hz (8 bit A/D) is shown in the upper left hand corner of FIG. 6 at 320. This is an acute human far-field EGM measured between the RV coil and the enclosure of a device as illustrated in FIG. 1. The 64 sample segment of data (254 milliseconds) was extracted from a continuous multi-channel recording using the technique of centering a morphology window around the bipolar sensed ventricular depolarization, as described in the above-cited Mader et al. patent. Below the Raw EGM segment on at 320 are wavelet representations of the Raw EGM using the largest wavelet coefficient at 322, the 10 largest wavelet coefficients at 324 and all 64 wavelet coefficients at 326. The thin lines 330 represent the wavelet(s) and associated amplitude(s), and the overlaid bold lines 332 trace the reconstructed waveforms, generated by performing the inverse DWT on the largest amplitude, the 10 largest amplitude and all 64 wavelet coefficients, respectively. The fidelity of the reconstructed waveform improves as more wavelets are used for the reconstruction. When all 64 wavelets are used, the original waveform is reconstructed accurately. The right hand side of FIG. 6 at 328 shows the six different time-scaled wavelets and the corresponding coefficient numbers $c_i$ as defined in FIG. 4 that form the shorthand notation for each wavelet coefficient and associated wavelet. The widest wavelet function in the upper right of FIG. 6 has two coefficient numbers (0 and 1) since two shifts of this wavelet function are needed to cover all 64 samples. Similarly, the narrowest wavelet (the "mother wavelet") has 32 coefficient numbers (32 through 63) corresponding to the 32 shifts needed to cover all 64 samples.

The Haar wavelet coefficients indicate how fast an average of a function changes at different scales. For example, coefficients (32–63) are just differences of the function values in consecutive points, coefficients (16–31) are differences of function average values over two points multiplied by two, coefficients (8–15) are differences of function average values over four points multiplied by four, and so on. The other information coded in the wavelet coefficients is exactly where the signal changes occur at each scale. For example, if a signal has a sharp peak in the center, only a few wavelet coefficients will be large, namely the ones that describe changes in signal at very fine scales and associated with the corresponding wavelets localized in the center of the analyzed signal. Furthermore, if the signal has a significant slow component, then in addition to few fine scale coefficients, a few larger scale coefficients will be significant in the wavelet expansion, and so on. Lower absolute value coefficients are less relevant, and in the approach taken by the present invention, will be filtered out and will not take part in further computation.

In addition to filtering based on the amplitude of the wavelet coefficients described above, it may be desired to filter out wavelet coefficients representing certain scales where unimportant signal information is represented. For example, the wavelet coefficients representing the widest wavelets may be set to zero to eliminate the contributions of the widest scale attributes of the signal. Other sets of wavelet coefficients representing a particular scale may be zeroed out to eliminate the contributions, depending on the application desired. In one preferred embodiment of this invention, the 48 point Haar wavelet transform described above is used, and the three highest numbered wavelet coefficients, (corresponding to the three widest wavelets) which do not provide significant signal discrimination, are set to 0 and thereby filtered out. Alternatives to this method may utilize all wavelet coefficients, or may filter out different sets corresponding to different scales in order to optimize discrimination performance.

Figure 7:
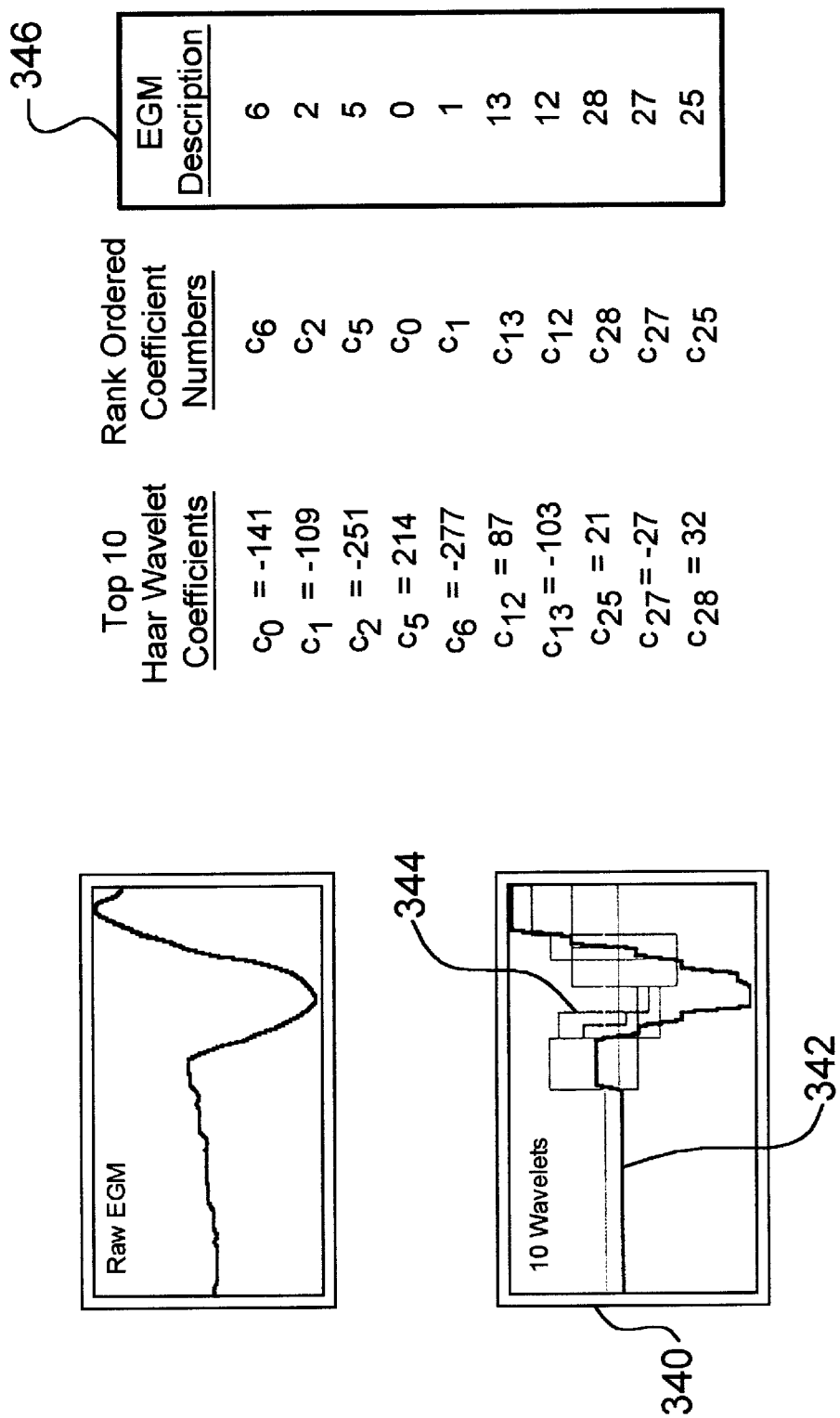
FIG. 7 is an illustration of the wavelet based waveform description utilized by the first embodiment of the present invention.

FIG. 7 illustrates how the DWT is used to form a waveform description for purposes of EGM waveform discrimination according to the first embodiment of the present invention. A DWT using the Haar function is computed based on the raw EGM input. The N most significant wavelets (preferably selected from the wavelets remaining after filtering by setting certain wavelet coefficients equal to zero as described above) are selected (N=10 in the example presented). This is done in the present embodiment by simply selecting the N largest absolute amplitude wavelet coefficients (corresponding to largest contribution). The decision to use 10 wavelets in this embodiment employing a 64 sample waveform was based on early analysis that indicated that fewer than 10 coefficients was not adequate to discriminate some waveforms, and using more than 10 coefficients did not significantly improve performance. In a more general case, the number of coefficients employed may be determined alternatively, for example by including only coefficients which have absolute amplitudes which exceed a predetermined percentage of the maximum absolute amplitude of all coefficients. In such an embodiment, the number of coefficients employed to form the waveform description of the template waveform could likewise be employed to subsequently form the waveform description unknown waveforms. Selection of only the wavelet coefficients having the largest amplitude coefficients provides an effective form of filtration and de-noising of the transformed waveform, with a minimum of computational complexity.

The graph at the lower left of FIG. 7 at 340 shows the waveform reconstructed (thick line 342) by selecting the 10 largest absolute amplitude wavelets (thin lines 344), and performing an inverse DWT. Also shown are the coefficient numbers and amplitudes for the 10 largest DWT coefficients, and the ranked ordered coefficient numbers (ranked by absolute amplitude). The EGM description is shown in the rightmost column at 346 and is given by the wavelet coefficient numbers, ordered by rank amplitude.

Figure 10:
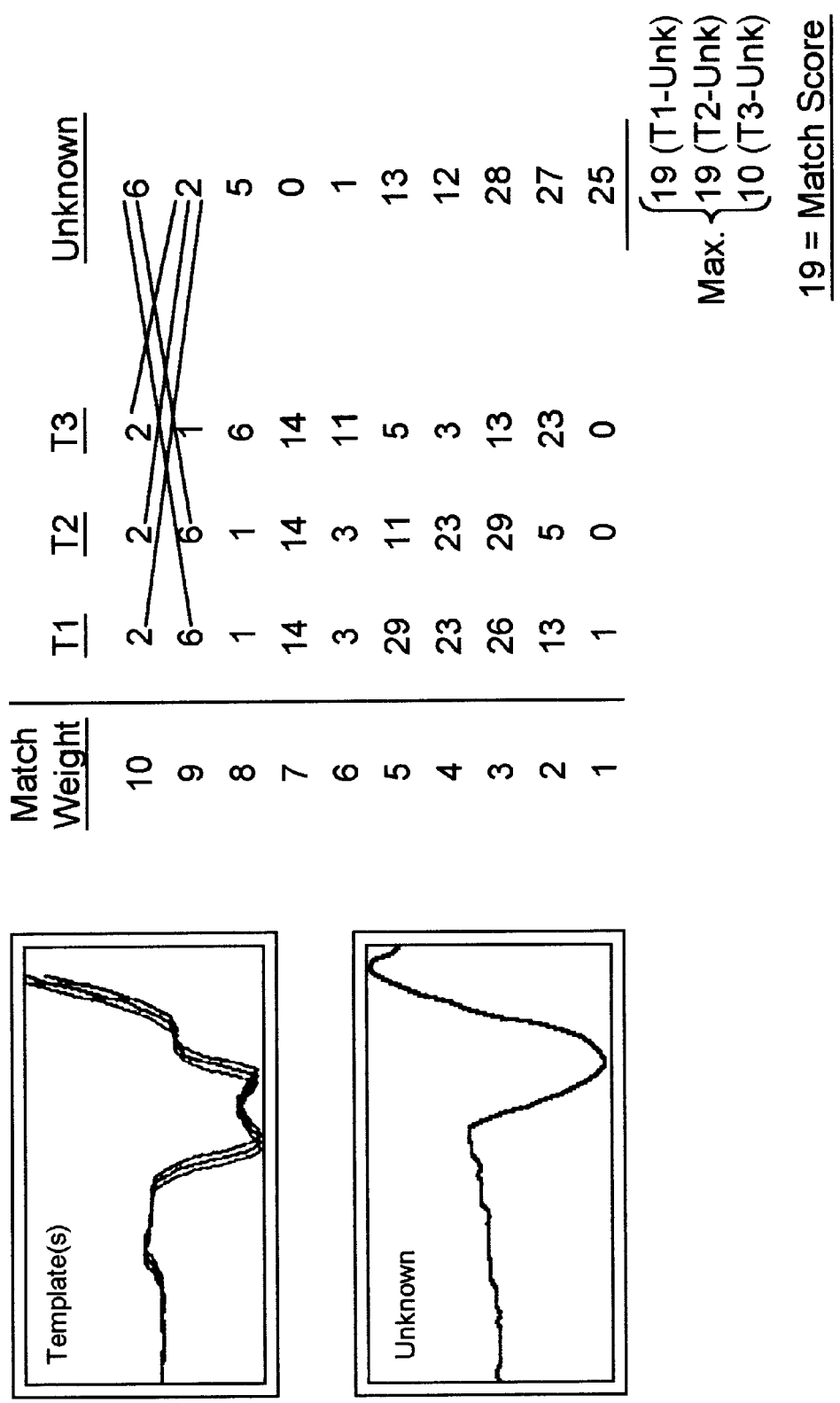
FIG. 10 is an illustration of waveform comparison method of the first embodiment of the present invention, employing multiple template waveform descriptions.

The EGM description of FIG. 7 is sensitive to shifts in the waveform relative to the beginning of the data buffer. In other words, slight variations in the fiducal or reference point, will cause the EGM description to vary slightly. For example, the point of bipolar ventricular sensing by the sense amplifier 514 (FIG. 2), as in the above-cited Mader, et al. patent may serve as the fiducial point. Alternatively, the fiducal point may be the positive or negative peak value of the stored sensed waveform, matched to the corresponding positive or negative peak of the template waveform. To account for slight changes in the fiducial point due to differences in the point of detection by the sense amplifier and/or due to phase differences associated with digitization of the waveform, the EGM description for the waveform used to generate the template may be formed using multiple shifted versions to account for slight changes in sensing during the arrhythmia. FIG. 10 illustrates a 64 sample EGM template waveform shifted +1 and −1 sample (4 msec.), and the resulting 3 sets of wavelet coefficients that describe the waveform. Alternatively, waveforms shifted +n, . . . +1, 0, −1 . . . −n data points might be employed, which would provided enhanced discrimination, but at a significant computational cost.

Figure 8:
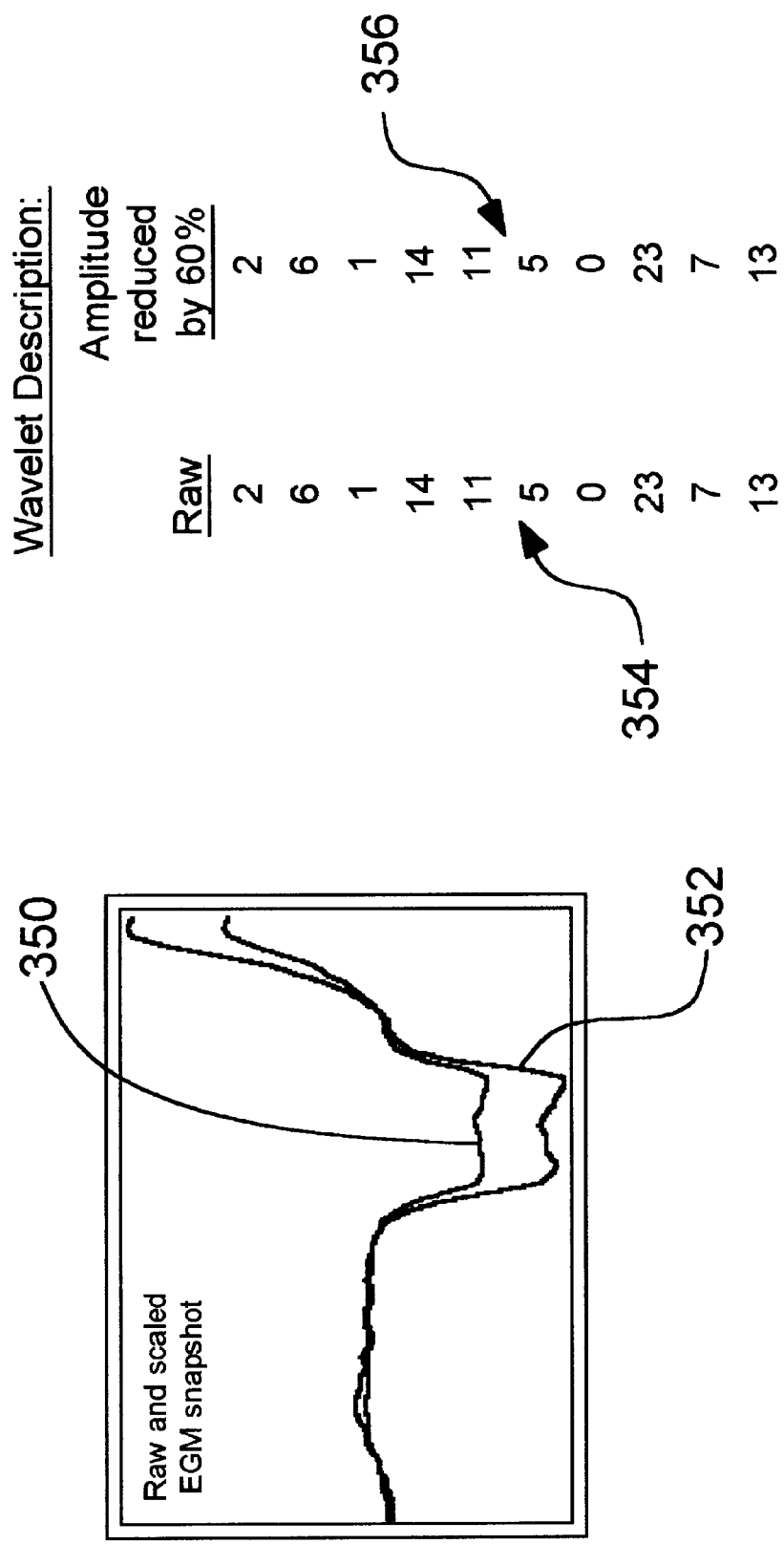
FIG. 8 is an illustration of the amplitude independence of the wavelet based waveform description utilized by the first embodiment of the present invention.

Using the wavelet coefficients for EGM morphology description, amplitude independence is achieved in this first embodiment of the invention, since only the relative amplitudes of the wavelet coefficients are used. FIG. 8 illustrates this result with a human EGM waveform (line352) and a version arbitrarily reduced in amplitude by 60% (line 350). Notice that the listed wavelet coefficient orders shown on the right hand side of FIG. 8 at 354, 356 are identical.

The purpose of the template matching functions of the present invention is to classify "unknown" EGM waveforms from the ongoing rhythm by comparing them to the stored templates. If the unknown waveform is a close match to one of the templates, the current beat or depolarization is classified as NORMAL, otherwise the current beat is classified as ECTOPIC. If the waveforms are predominately ECTOPIC, then the rhythm is NOT an SVT, and ventricular therapies are typically delivered when the rate detection criteria are satisfied, as noted above. The determination of whether or not a waveform matches the template is made by comparing a match metric to a match threshold. If the match metric exceeds the match threshold, then the waveform is a close match to the template and the EGM morphology should be considered to be NORMAL. For this aspect of the present invention, the wavelet transform serves as a means of describing the salient features of the waveforms in a relatively small set of wavelet coefficients. The technique for generating an EGM morphology description based on N wavelet coefficients entails computing the DWT of the raw waveform and rank ordering the N largest wavelet coefficients, as described above. This process is the same for the "template" waveforms and for the "unknown" waveforms. The template descriptions are stored in memory. For each template, there will be, for example, 10 wavelet coefficient numbers $c_i$, each with a corresponding rank based on its absolute amplitude, where rank=1 is given to the smallest absolute amplitude and rank=N is given to the largest absolute amplitude. The rank of the each template coefficient is used as a match weight in computing the match metric, so the ranks must be stored with the template coefficients.

Figure 9:
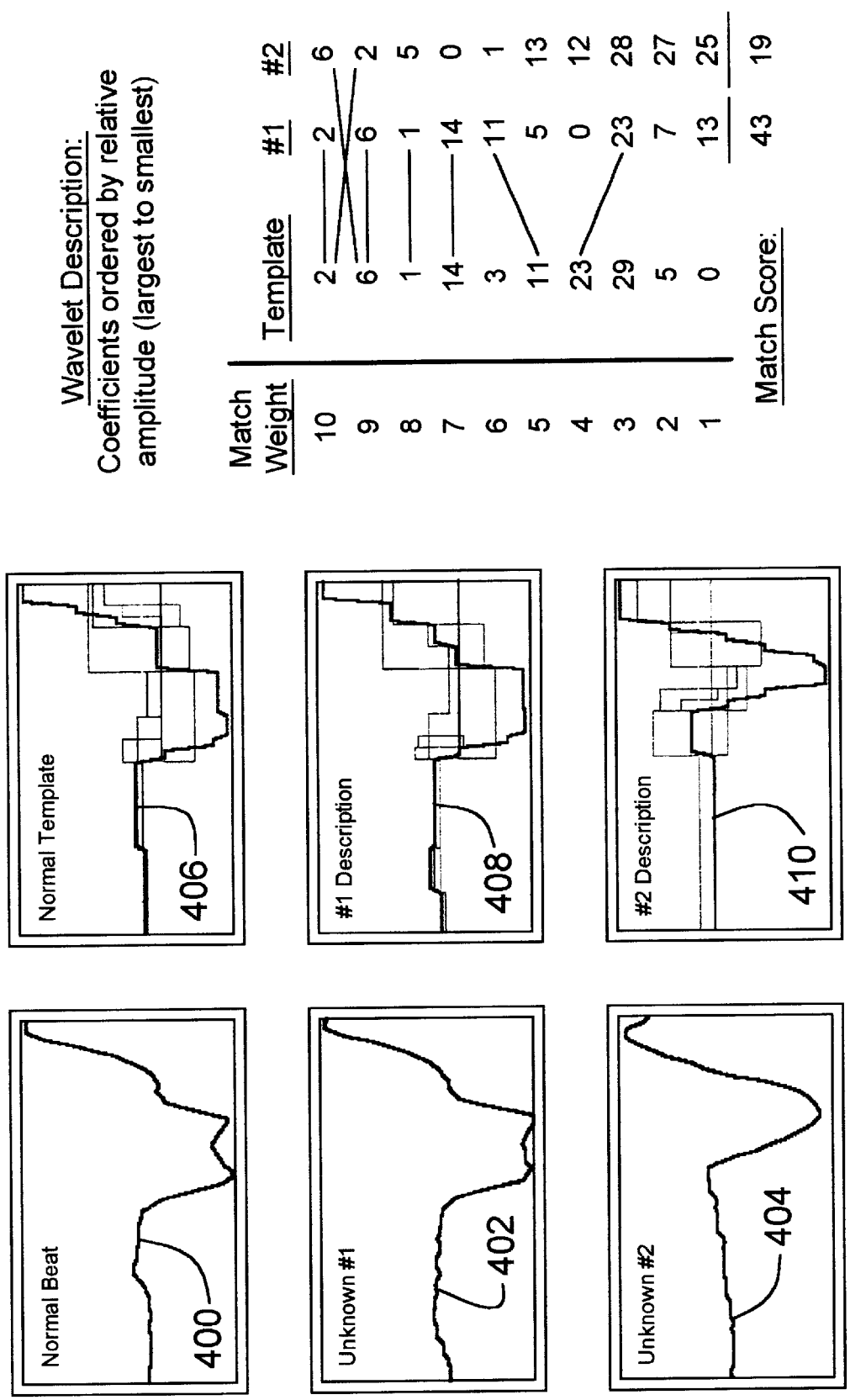
FIG. 9 is an illustration of the waveform comparison method of the first embodiment of the present invention, employing a single template waveform description.

FIG. 9 illustrates the template matching function of the first embodiment of the present invention, assuming a single template waveform description from a normal EGM morphology is stored in memory. The upper left hand side of FIG. 9 shows at 400 a normal beat used as the template, with the rank ordered wavelet coefficient numbers for the normal template listed from largest to smallest absolute amplitude under the column labeled Template (N=10 in this example). Similarly, wavelet coefficient numbers rank-ordered by relative absolute amplitudes are listed for two unknown waveforms, #1(402) and #2(404). The match weights for the ordered coefficient numbers are listed under the Match Weight column and correspond to the relative ranking of the listed wavelet coefficients (highest absolute amplitude coefficient, match weight 10, lowest absolute amplitude coefficient, match weight 1,. FIG. 9 also shows the waveforms reconstructed (lines 406, 408, 410) by selecting the 10 largest absolute amplitude wavelets and performing an inverse DWT.

The mechanism for generating the match metric (match_score) is also illustrated in FIG. 9. The match_score is computed based on whether the unknown description has a wavelet coefficient number that is exactly the same as one of the template wavelet coefficient numbers. If the wavelet coefficient numbers match AND the coefficients have similar absolute amplitude ranking (within +1 or −1 in rank), then the match weight for the template coefficient is added to the match metric. As can be seen for the example, Unknown #1 has more wavelet coefficient matches, and thus a higher overall match score (match_score=43) than Unknown #2 (match_score=19). The classification of each beat as NORMAL or ECTOPIC is achieved by comparing the match_score to a match threshold; if match_score>match threshold, the beat is NORMAL and if match_score<match threshold, the beat is ECTOPIC. Assuming the match threshold is 41 for the example in FIG. 9, Unknown #1 is classified as NORMAL and Unknown #2 is classified as ECTOPIC. As can be seen by visual inspection of the waveform morphologies (left hand side of FIG. 9), Unknown #1 has a morphology more similar to the template than Unknown #2.

The following pseudo-code explains the steps that are performed by the microprocessor 524 (FIG. 2) in performing the comparison of the stored transformed waveform to a single template during EGM morphology analysis of a tachyarrhythmia, according to the first embodiment of the present invention:

1. Extract the EGM window of data samples ("unknown" waveform)
2. Compute the DWT of the unknown waveform
3. Find the unknown EGM description by rank ordering the N largest absolute amplitude wavelet coefficients.
4. Compute the match_score as follows:

Initialize match_score=0

For each template wavelet coefficient, $c_i$:
     If {the unknown description has $c_i$ as one of its elements}, then
       If {abs[(rank of template $c_i$)−(rank of unknown $c_i$)]=1}
       then
         match_score=match_score+(rank of template ci)
       endIf
     endIf
   Next template wavelet coefficient.
5. If (match_score=match threshold) Then
     (EGM_morphology=NORMAL)
   Else (EGM_morphology=ECTOPIC)
   endIF This matching mechanism is easily extended to the case of more than one template waveform description. In the practical case, it is likely that it will be desirable to have more than one template in order to avoid inappropriate detection due to SVTs that result in slightly different EGM morphologies due to detection by the sense amp 514 (FIG. 2) at slightly different times and to solve the shift-dependence problem with wavelet transform. In the case presented in FIG. 10, three-template waveforms were generated by shifting a single waveform −1 and +1 sample and performing the Haar transform on the shifted waveforms. In the case of multiple templates, a match_score is computed for each template. The NORMAL vs. ECTOPIC decision is based on the best match, indicated by the maximum match_score as shown in the FIG. 10.

The general philosophy behind the integration of rate-base detection and EGM morphology in as described in the above-cited Mader, et al. patent was to use the EGM width decision to augment the rate-based decision once the VT counter reaches the programmed number of intervals for detection (NID). In the case of the EGM width algorithm, if at least 6 of the last 8 beats had WIDE EGM width, the rhythm would be classified as VT and therapies are delivered. However, if 3 or more of the last 8 beats had NARROW EGM width, the VT counter was reset and detection continues (with EGM width evaluated again once the VT counter reaches NID). This approach has been useful in eliminating false positive decision during SVTs with intermittent aberrancy or PVCs, and allowed for 1 or 2 sinus capture beats during a VT episode. In one implementation of the present invention, this aspect of the wavelet based EGM morphology discrimination method of the present invention may be the same as for the EGM width discrimination method of the Mader, et al. patent. In such an embodiment, for a rhythm to be classified as VT, at least X of the last Y beats (e.g. 6 of 8) must have ECTOPIC EGM morphology, VT therapy will not be delivered Y−X+1 (e.g. 3) or more of the last Y beats have NORMAL EGM morphology. Unlike the method employed in the Mader, et al. patent, it is believed desirable in some embodiments to not reset the rate based VT detection criteria (e.g. the VT Counter) when a NORMAL EGM morphology is seen, but rather to continue to evaluate the EGM morphology decision on every ventricular beat where the VT counter is satisfied. Such an embodiment is illustrated in FIG. 3B, discussed above.

As noted above, the waveform discrimination capabilities of the present invention may also usefully be employed in conjunction with tachyarrhythmia detection mechanisms other than those described above, based upon depolarization rates, depolarization intervals and/or depolarization orders. The specific additional criteria employed in conjunction with the waveform discrimination methods of the present invention are not believed critical to its practice, as the discrimination methods of the present invention are believed to offer the opportunity for enhancement of virtually any tachyarrhythmia detection methodology.

Wavelet Based EGM Morphology Discrimination Algorithm—Second and Third Embodiments In the second and third embodiments of the present invention, the template and unknown waveforms are acquired, transformed and filtered generally as described above, but are compared using an area of distance (AD) or a correlation waveform analysis (CWA) metric. These methods Of comparing unknown and template waveforms, which would require an undesirably large number of computations if performed on all data points within digitized template and unknown waveforms become more manageable when applied to transformed and filtered waveforms. Unlike the first embodiment, the AD and CWA metrics do require amplitude normalization, as discussed below. The fiducial points used for alignment of the template and unknown waveforms are preferably either the positive or negative peaks of the unknown and template waveforms. The calculations associated with the storage, transformation and comparison of the template and unknown waveforms are performed by the microprocessor 524 (FIG. 2), and the waveform comparison methods of the second and third embodiments may simply be substituted for the waveform comparison method of the first embodiment, in a device as otherwise described above.

The CWA and AD metrics require minimization of the distance between the two waveforms being compared.

However, for similar signals it is "safe" to assume that if the two signals are properly aligned, the corresponding distance will take it's minimal value somewhere around zero shift. Therefore, in the second and third embodiments of the invention, like the first embodiment described above, the device first performs the waveform alignment and then looks for the minimum of the applied metric between the two waveforms shifted by (−n, . . . , −1,0,1, . . . , n) time units, where n is the maximum shift. For implementation of the second and third embodiments ICDs, the value of n may be 1, resulting in the use of three templates, as in the first embodiment discussed above. The alignment of the unknown and template waveforms at zero shift is done by aligning the positive or negative peaks in the template and unknown waveforms.

In the second and third embodiments, filtration of the template and unknown waveforms may be accomplished by simply setting to zero all wavelet coefficients that are smaller than the maximum (positive or negative) wavelet coefficient divided by a filter factor (for example, 8, 16 or 32). Such divisions require only arithmetic shift CPU instructions and may be performed efficiently in the microprocessor types typically employed in ICDs. Additionally or alternatively filtration may also be accomplished by simply setting certain pre-designated wavelet coefficients to zero as discussed above. Normalization is required in order to make minimal distances between two signals that are scaled copies of each other. This normalization can be done very efficiently if it is performed in the wavelet domain. Instead of normalizing the unknown waveform in the time domain, the second and third embodiments of the present invention normalize its wavelet image, which requires only a fraction amount of computations, since the number of wavelet coefficients surviving filtration will be small.

In the method of the second and third embodiments of the present invention, the distance is computed between the wavelet image of the unknown waveform $\omega_i$ and wavelet images of the template waveform $t_i$, typically shifted by plus or minus one position in time. If the minimum distance is zero, then the two waveforms are scaled copies of each other. In practice the minimum will seldom be exactly zero. In order to make decision about how small the distance is, the microprocessor divides the calculated distance by the corresponding norm of the template wave to provide distance normalization. If the resulting number is significantly smaller than 1, the waves are considered to be to be similar. The norm of the template wave is defined as the calculated distance between tie template wave and the zero signal (signal consisting of zero values).

The correlation waveform analysis (CWA) function as traditionally performed computes the correlation function between two signals as follows, where $t_{i−j}$ are the template waveforms and $w_i$ is the unknown waveform:

$$CF = \frac{\sum_i t_{i-j} \cdot w_i}{\|t\|\|w\|}$$

where $\|t\|=\Sigma t_i^2$ and $\|w\|=\Sigma w_i^2$ and j is the relative shift between the signals.

Using this method one looks for maximum correlation between the signals by scanning through the shifted signals. If CF=1, then the signals are totally correlated (one is just a scaled copy of another).

If one tries to implement this computation in an ICD, many multiplications are required, making this computation too computationally expensive. However, the number of multiplications can be significantly reduced by performing the analysis in the wavelet domain. After transforming the signal into the wavelet domain and filtering the transformed signal by removing low amplitude coefficients, the number of wavelet coefficients remaining will be much smaller than the number of samples in the time domain, reducing computational complexity. In addition, further reduction in computational complexity can be accomplished by calculating the CWA metric by means of calculation and minimization of the distance between the unknown waveform and the template waveforms as follows:

$$d_j^2 = \sum_i (t_{i-j} - w_i)^2$$

The calculation and minimization of the distance between the unknown and template waveforms can be efficiently performed in an ICD. The calculations performed by the microprocessor are set forth in more detail below. This method corresponds to the CWA metric in the wavelet domain, because it is mathematically equivalent to it.

The wavelet transforms of templates and the unknown are generated as described above in conjunction with the first embodiment, $$\tilde{t}_j(i)=WT[t_{i-j}],$$

$$\tilde{w}(i)=WT[w_i].$$

where $WT[f_i]$ denotes wavelet transform of the wave $f_i$.

The unknown waveform is filtered and normalized as follows:

$$\tilde{w}(i) = \tilde{w}(i), \text{ if } \tilde{w}(i) > \frac{\max_k (|\tilde{w}(k)|)}{\text{filter factor}}, \text{ otherwise } 0$$

$$\tilde{\tilde{w}}(i) = \frac{N}{A}\tilde{w}(i)$$

where N is the amplitude of the normalized wave and A is the amplitude of the unknown and the filter factor is, for example, 8, 16, 32, etc as described above. The templates $t_i$ are normalized to the same amplitude N.

For each shifted template the norm is defined as follows:

$$n_j = \sum_i |\tilde{t}_j(i)|^2$$

The normalized distances are defined as follows:

$$d_j = \frac{\sum_i (\tilde{t}_j(i) - \tilde{\tilde{w}}(i))^2}{n_j}$$

The measure of similarity between the waveforms is calculated as follows:

$$d = \min_j (d_j)$$

In this implementation, the value "d" is compared by the microprocessor to a threshold that is programmed by the physician to achieve the desired discrimination performance. If d is greater than the threshold, the waveforms are found to be dissimilar. Assuming that the templates are of normal waveforms, the unknown waves found to be similar to the template will be considered NORMAL and may be employed in the same fashion as described above in conjunction with the first embodiment.

An alternative and computationally simpler method of determining the similarity between unknown waveforms and template waveforms is the area of difference (AD) metric, which, like the CWA metric described above, calculates and minimizes distances dj between the unknown waveform wj and the template waveform $t_{ji}$ shifted by j points, as follows:

$$d_j = \sum_i |t_{i-j} - w_i|$$

In this case, the distances are computed as absolute values rather than squares, which makes it easier to compute. One can apply the AD metric directly in the wavelet domain, but in this case it is not equivalent to the AD metric applied in the time domain. This metric nonetheless performs well for EGM morphology discrimination in the wavelet domain. It also is less computationally costly that the CWA metric, and is desirable for this reason.

The steps needed to compute the AD metric correspond to those described above in conjunction with the CWA metric, as follows:

The wavelet transforms of templates and the unknown are generated as described above in conjunction with the first embodiment, $$\tilde{t}_j(i) = WT[t_{i-j}],$$

$$\tilde{w}(i) = WT[w_i].$$

where $WT[f_i]$ denotes wavelet transform of the wave $f_i$.

The unknown waveform is filtered and normalized as follows:

$$\tilde{w}(i) = \tilde{w}(i), \text{ if } \tilde{w}(i) > \frac{\max_k(|\tilde{w}(k)|)}{\text{filter factor}}, \text{ otherwise } 0$$

$$\tilde{\tilde{w}}(i) = \frac{N}{A}\tilde{w}(i)$$

where N is the amplitude of the normalized wave and A is the amplitude of the unknown. The templates $t_i$ are normalized to the same amplitude N.

For each shifted template the norm is defined as follows:

$$n_j = \sum_i |\tilde{t}_j(i)|$$

The normalized distances are defined as follows:

$$d_j = \frac{\sum_i |\tilde{t}_j(i) - \tilde{\tilde{w}}(i)|}{n_j}$$

The measure of similarity between the waveforms is calculated as follows:

$$d = \min_j(d_j)$$

If this number is smaller than a pre-selected threshold, the microprocessor designates the waveforms as similar, otherwise they are found to be dissimilar. Assuming that the templates are of normal waveforms, the unknown waves found to be similar to the template will be considered NORMAL and may be employed in the same fashion as described above in conjunction with the first embodiment.

In conjunction with the above disclosure, we claim:

1. A device for monitoring heart rhythms, comprising:
    means for storing digitized electrogram segments including signals indicative of depolarizations of a chamber or chamber of a patient's heart;
    means for transforming the digitized signals into signal wavelet coefficients;
    means for identifying higher amplitude ones of the signal wavelet coefficients; and
    means for generating a match metric corresponding to the higher amplitude ones of the signal wavelet coefficients and a corresponding set of template wavelet coefficients derived from signals indicative of a heart depolarization of known type, and identifying the heart rhythms in response to the match metric.

2. The device of claim 1, wherein the transforming means comprises means for transforming the digitized signals using a wavelet transform to obtain the signal wavelet coefficients.

3. A device for monitoring heart rhythms, comprising:
    means for storing digitized electrogram segments including signals indicative of depolarizations of a chamber or chamber of a patient's heart;
    means for transforming the digitized signals into signal wavelet coefficients;
    means for identifying higher amplitude ones of the signal wavelet coefficients; and
    means for comparing the higher amplitude ones of the signal wavelet coefficients with a corresponding set of template wavelet coefficients derived from signals indicative of a heart depolarization of known type, wherein the transforming means comprises means for transforming the digitized signals using a Haar wavelet transform to obtain the signal wavelet coefficients.

4. The device of claim 3, wherein the transforming means comprises means for transforming the digitized signals using a simplified, weighted Haar wavelet transform to obtain the signal wavelet coefficients without performing steps of division by the square root of two.

5. The device of claim 1 or claim 2 or claim 3 or claim 4 further comprising means for filtering the transformed signals by deleting lower amplitude ones of the signal wavelet coefficients.

6. The device of claim 1 or claim 2 or claim 3 or claim 4 further comprising means for filtering the transformed signals by deleting the signal wavelet coefficients corresponding to selected wavelets.

7. The device of claim 6 wherein the generating means comprises means for ordering the signal wavelet coefficients and the template wavelet coefficients by absolute amplitude and means for comparing the orders of the signal wavelet coefficients and the template wavelet coefficients.

8. The device of claim 6 wherein the generating means comprises means for calculating distances between the signal wavelet coefficients and the wavelet coefficients.

9. The device of claim 1 or claim 2 or claim 3 or claim 4 further comprising means for filtering the transformed signals by setting lower amplitude ones of the signal wavelet coefficients equal to zero.

10. The device of claim 9 wherein the generating means comprises means for ordering the signal wavelet coefficients and the template wavelet coefficients by absolute amplitude and means for comparing the orders of the signal wavelet coefficients and the template wavelet coefficients.

11. The device of claim 9 wherein the generating means comprises means for calculating distances between the signal wavelet coefficients and the template wavelet coefficients.

12. The device of claim 1 or claim 2 or claim 3 or claim 4 wherein the generating means comprises means for comparing only higher amplitude ones of the signal wavelet coefficients.

13. The device of claim 12 wherein the generating means comprises means for ordering the signal wavelet coefficients and the template wavelet coefficients by absolute amplitude and means for comparing the orders of the signal wavelet coefficients and the template wavelet coefficients.

14. The device of claim 12 wherein the generating means comprises means for calculating distances between the signal wavelet coefficients and the template wavelet coefficients.

15. The device of claim 1 or claim 2 or claim 3 or claim 4 wherein the generating means comprises means for ordering the signal wavelet coefficients and the template wavelet coefficients by absolute amplitude and means for comparing the orders of the signal wavelet coefficients and the template wavelet coefficients.

16. The device of claim 1 or claim 2 or claim 3 or claim 4 wherein the generating means comprises means for calculating distances between the signal wavelet coefficients and the template wavelet coefficients.

17. The device of claim 1 or claim 2 or claim 3 or claim 4 wherein the transforming means comprises a microprocessor.

18. A method of monitoring heart rhythms, comprising:
    storing digitized electrogram segments including signals indicative of depolarizations of a chamber or chamber of a patient's heart;
    transforming the digitized signals into signal wavelet coefficients;
    identifying higher amplitude ones of the signal wavelet coefficients;
    generating a match metric corresponding to the higher amplitude ones of the signal wavelet coefficients with a corresponding set of template wavelet coefficients derived from signals indicative of a heart depolarization of known type; and
    identifying the heart rhythms in response to the match metric.

19. The method of claim 18, wherein transforming the digitized signals comprises transforming the digitized signals using a wavelet transform to obtain the signal wavelet coefficients.

20. A method of monitoring heart rhythms, comprising;
    storing digitized electrogram segments including signals indicative of depolarizations of a chamber or chamber of a patient's heart;
    transforming the digitized signals into signal wavelet coefficients;
    identifying higher amplitude ones of the signal wavelet coefficients; and
    comparing the higher amplitude ones of the signal wavelet coefficients with a corresponding set of template wavelet coefficients derived from signals indicative of a heart depolarization of known type, wherein transforming the digitized signals comprises transforming the digitized signals using a Haar wavelet transform to obtain the signal wavelet coefficients.

21. The method of claim 18, wherein the transforming the digitized signals comprises transforming the digitized using a simplified, weighted Haar wavelet transform to obtain the signal wavelet coefficients without performing steps of division by the square root of two.

22. The method of claim 18 or claim 19 or claim 20 or claim 21 further comprising filtering the transformed signals by deleting lower amplitude ones of the signal wavelet coefficients.

23. The method of claim 18 or claim 19 or claim 20 or claim 21 further comprising filtering the transformed signals by deleting the signal wavelet coefficients corresponding to selected wavelets.

24. The method of claim 23 wherein generating a match metric comprises ordering the signal wavelet coefficients and the template wavelet coefficients by absolute amplitude and comparing the orders of the signal wavelet coefficients and the template wavelet coefficients.

25. The method of claim 23 wherein generating a match metric comprises calculating distances between the signal wavelet coefficients and the template wavelet coefficients.

26. The method of claim 18 or claim 19 or claim 20 or claim 21 further comprising filtering the transformed signals by setting lower amplitude ones of the signal wavelet coefficients equal to zero.

27. The method of claim 26 wherein generating a match metric comprises ordering the signal wavelet coefficients and the template wavelet coefficients by absolute amplitude and comparing the orders of the signal wavelet coefficients and the template wavelet coefficients.

28. The method of claim 26 wherein generating a match metric comprises calculating distances between the signal wavelet coefficients and the template wavelet coefficients.

29. The method of claim 18 or claim 19 or claim 20 or claim 21 wherein generating a match metric comprises comparing only higher amplitude ones of the signal wavelet coefficients.

30. The method of claim 29 wherein generating a match metric comprises ordering the signal wavelet coefficients and the template wavelet coefficients by absolute amplitude and comparing the orders of the signal wavelet coefficients and the template wavelet coefficients.

31. The method of claim 30 wherein generating a match metric comprises calculating distances between the signal wavelet coefficients and the template wavelet coefficients.

32. The method of claim 18 or claim 19 or claim 20 or claim 21 wherein generating a match metric comprises ordering the signal wavelet coefficients and the template wavelet coefficients by absolute amplitude and comparing the orders of the signal wavelet coefficients and the template wavelet coefficients.

33. The device of claim 18 or claim 19 or claim 20 or claim 21 wherein generating a match metric comprises means calculating distances between the signal wavelet coefficients and the template wavelet coefficients.

34. The method of claim 16 or claim 17 or claim 18, wherein transforming the digitized signal comprises transforming the digitized signal using a microprocessor.

35. The device of claim 1, wherein each of the signal wavelet coefficients and the template wavelet coefficients have respective match weights corresponding to a relative ranking, the generating means adding the match weights of the signal wavelet coefficients to the match metric in response to signal wavelet coefficient numbers of the signal wavelet coefficients matching template wavelet coefficient numbers of the template wavelet coefficients, and the match weight of the signal wavelet coefficient being approximately equal to the match weight of the template wavelet coefficients.

36. The device of claim 35, wherein the generating means compares the match metric to a match threshold and identifies the heart rhythms as having a first morphology in response to the match metric being greater than the match threshold, and as having a second morphology in response to the match metric being less than the match threshold.

37. The method of claim 18, wherein generating a match metric comprises adding match weights of the signal wavelet coefficients to the match metric in response to signal wavelet coefficient numbers of the signal wavelet coefficients matching template wavelet coefficient numbers of the template wavelet coefficients, and the match weights of the signal wavelet coefficients being approximately equal to match weights of the template wavelet coefficients, the match weights of the signal wavelet coefficients and the template wavelet coefficients corresponding to a relative ranking of the signal wavelet coefficients and the template wavelet coefficients, respectively.

38. The method of claim 37, wherein identifying the heart rhythms compares the match metric to a match threshold and identifies the heart rhythms as having a first morphology in response to the match metric being greater than the match threshold, and as having a second morphology in response to the match metric being less than the match threshold.

* * * * *